(12) United States Patent
Ogasahara

(10) Patent No.: US 11,387,279 B2
(45) Date of Patent: Jul. 12, 2022

(54) IMAGING ELEMENT, ELECTRONIC APPARATUS, AND METHOD OF DRIVING IMAGING ELEMENT

(71) Applicant: SONY SEMICONDUCTOR SOLUTIONS CORPORATION, Kanagawa (JP)

(72) Inventor: Takayuki Ogasahara, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 17/055,702

(22) PCT Filed: Apr. 24, 2019

(86) PCT No.: PCT/JP2019/017430
§ 371 (c)(1),
(2) Date: Nov. 16, 2020

(87) PCT Pub. No.: WO2019/220897
PCT Pub. Date: Nov. 21, 2019

(65) Prior Publication Data
US 2021/0193739 A1 Jun. 24, 2021

(30) Foreign Application Priority Data
May 18, 2018 (JP) .............................. JP2018-096530

(51) Int. Cl.
*H01L 27/30* (2006.01)
*A61B 1/04* (2006.01)

(52) U.S. Cl.
CPC ............ *H01L 27/307* (2013.01); *A61B 1/041* (2013.01)

(58) Field of Classification Search
CPC ............ H01L 27/307; H01L 27/14627; H01L 27/1464; H01L 27/14647; H01L 27/14638;
(Continued)

(56) References Cited

U.S. PATENT DOCUMENTS

| 2007/0012955 A1* | 1/2007 | Ihama | H01L 51/448 257/233 |
| 2011/0032376 A1 | 2/2011 | Takizawa | |

(Continued)

FOREIGN PATENT DOCUMENTS

| JP | 2011-029337 A | 2/2011 |
| JP | 2011-040518 A | 2/2011 |

(Continued)

OTHER PUBLICATIONS

International Search Report and Written Opinion of PCT Application No. PCT/JP2019/017430, dated Jul. 16, 2019, 11 pages of ISRWO.

*Primary Examiner* — Thanh Luu
*Assistant Examiner* — Monica T Taba
(74) *Attorney, Agent, or Firm* — Chip Law Group

(57) ABSTRACT

An imaging element according to an embodiment of the present disclosure includes a first photoelectric conversion section and a second photoelectric conversion section that are stacked in order from light incident side and that selectively detect and photoelectrically convert light beams of different wavelength bands, and the second photoelectric conversion section is disposed at an interval narrower than a pixel pitch of the first photoelectric conversion section.

14 Claims, 26 Drawing Sheets

(58) Field of Classification Search
CPC ......... H01L 27/14614; H01L 27/14603; H01L 27/14667; A61B 1/041; H04N 5/36961; H04N 9/04563; H04N 5/347
See application file for complete search history.

(56) References Cited

U.S. PATENT DOCUMENTS

| | | | | |
|---|---|---|---|---|
| 2013/0341750 | A1* | 12/2013 | Ichikawa | H01L 27/14647 257/440 |
| 2015/0187843 | A1* | 7/2015 | Hatano | H04N 5/369 257/40 |
| 2015/0255498 | A1 | 9/2015 | Sugiura | |
| 2016/0050359 | A1* | 2/2016 | Nakata | G03B 13/36 250/201.2 |
| 2017/0257587 | A1* | 9/2017 | Hatano | H01L 27/14623 |
| 2019/0019835 | A1* | 1/2019 | Tanaka | H04N 5/374 |

FOREIGN PATENT DOCUMENTS

| | | |
|---|---|---|
| JP | 2015-170620 A | 9/2015 |
| JP | 2017-017563 A | 1/2017 |
| WO | 2014/027588 A1 | 2/2014 |
| WO | 2017/002715 A1 | 1/2017 |

* cited by examiner

[FIG. 1]
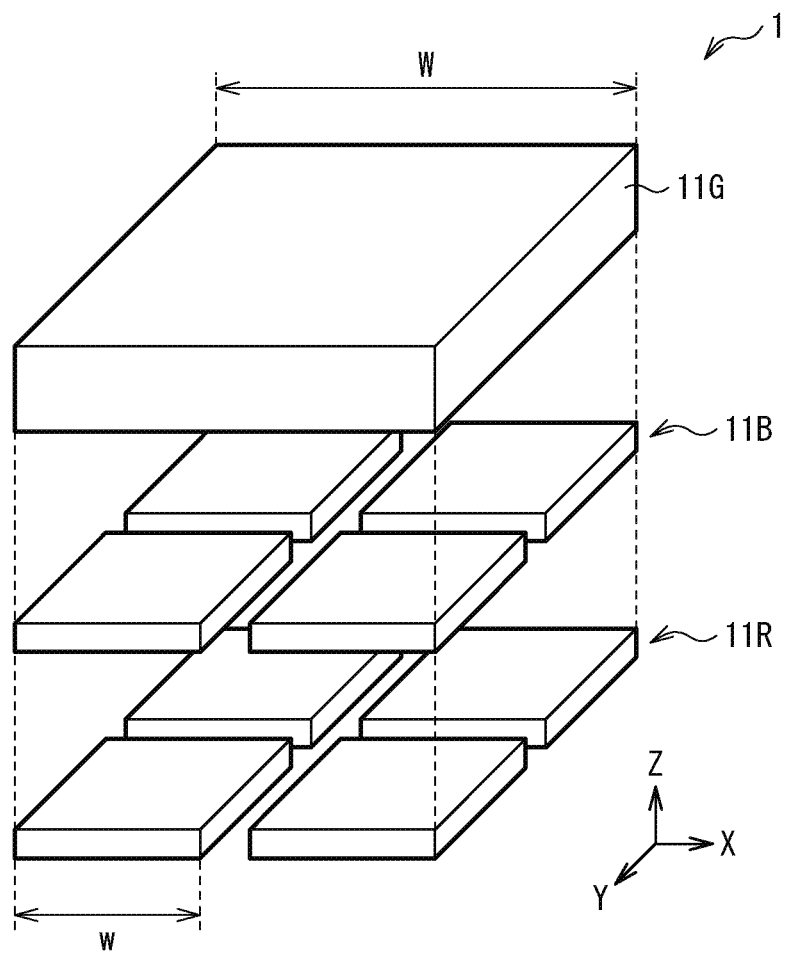

[FIG. 2]
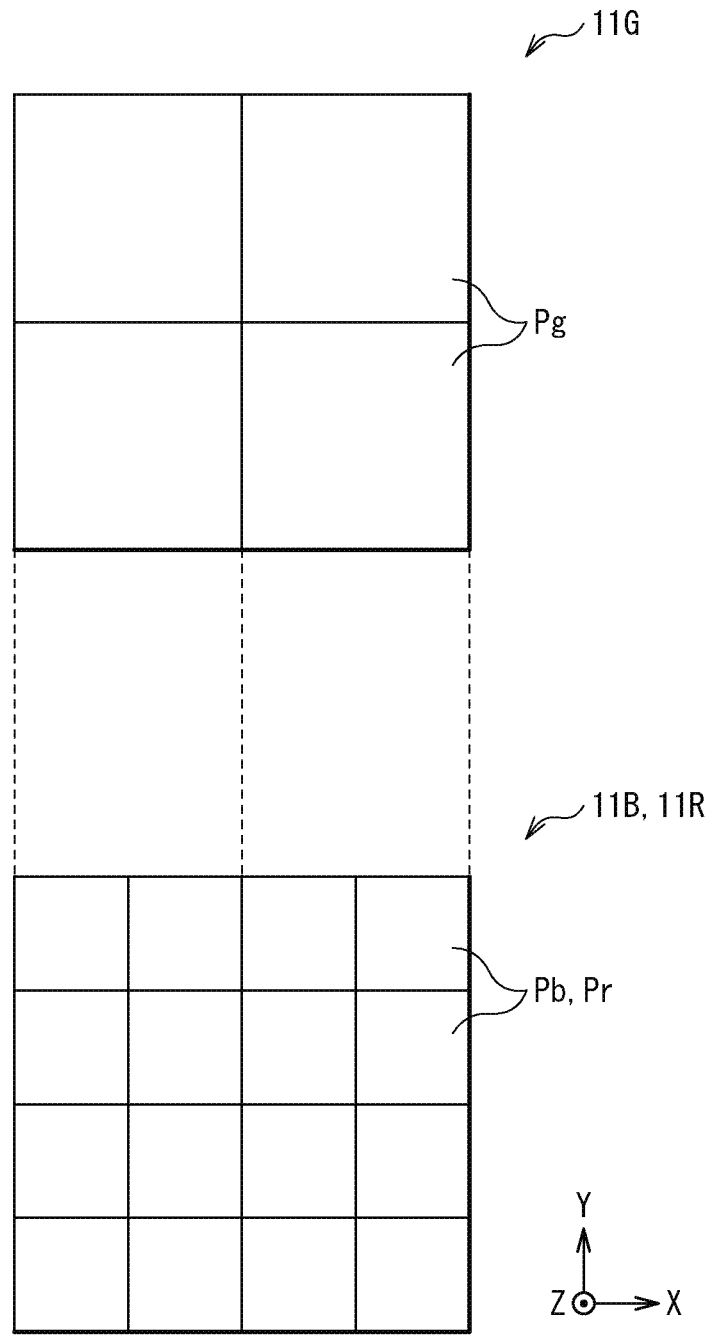

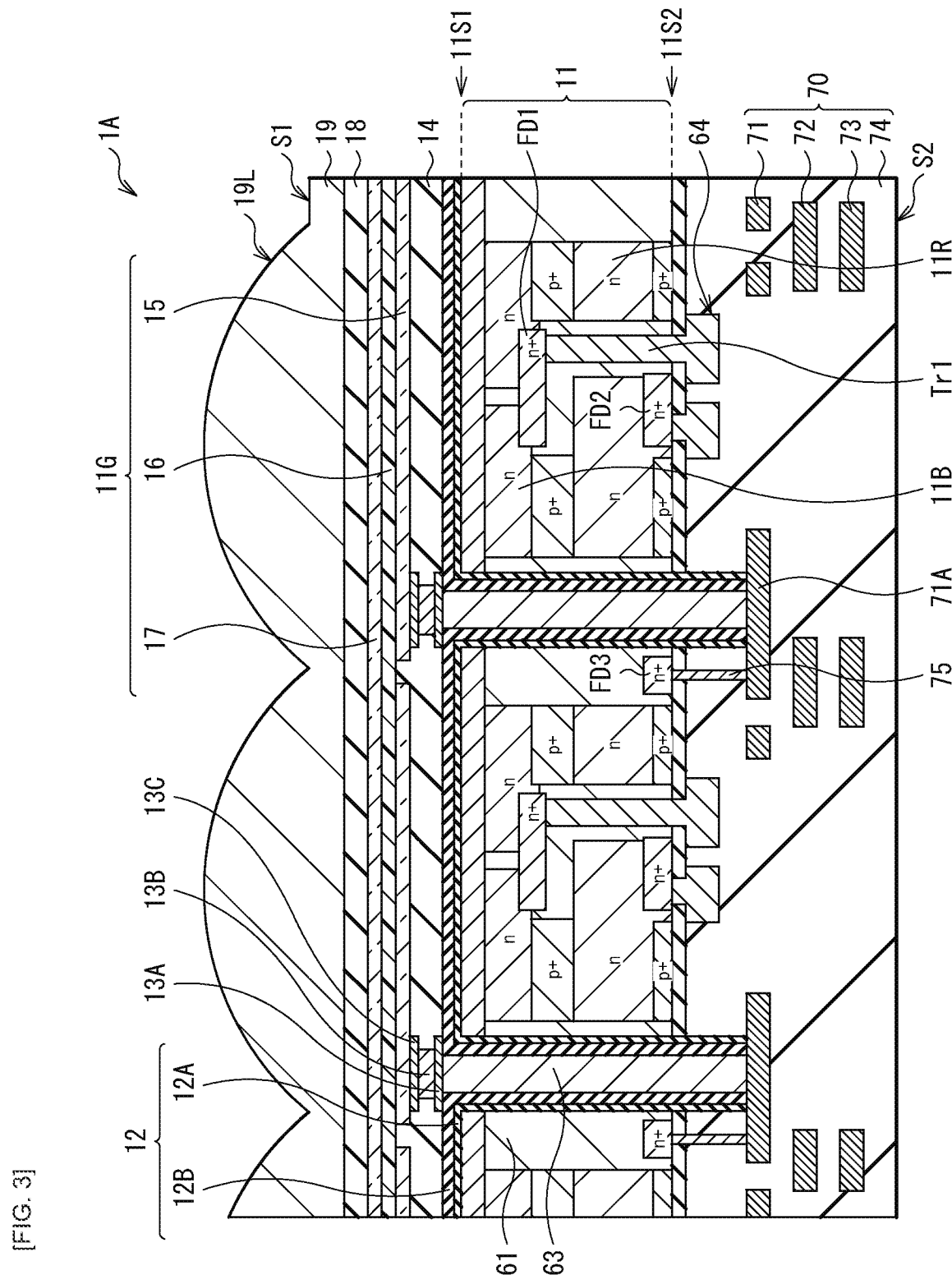
[FIG. 3]

[FIG. 4A]
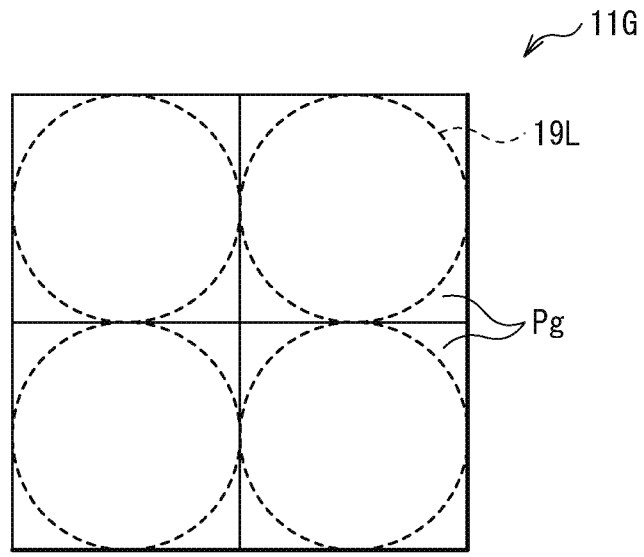
[FIG. 4B]
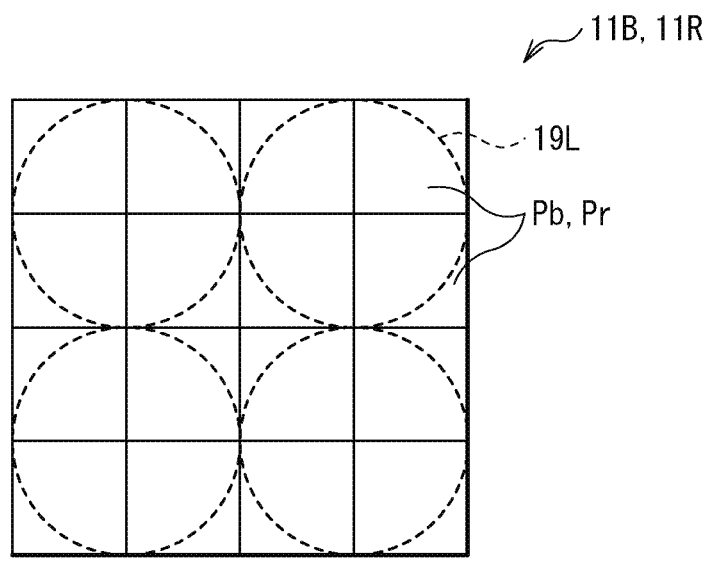

[FIG. 5A]
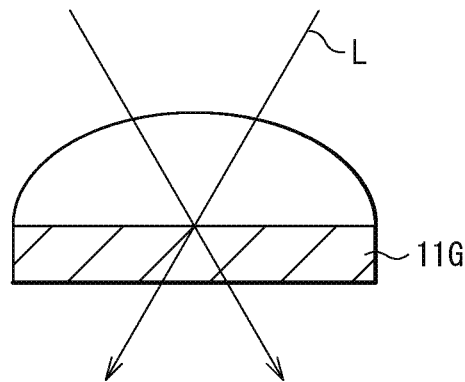
[FIG. 5B]
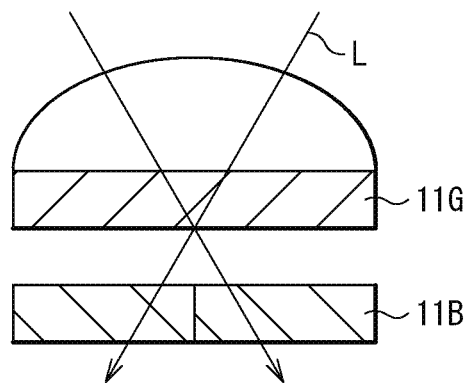
[FIG. 5C]
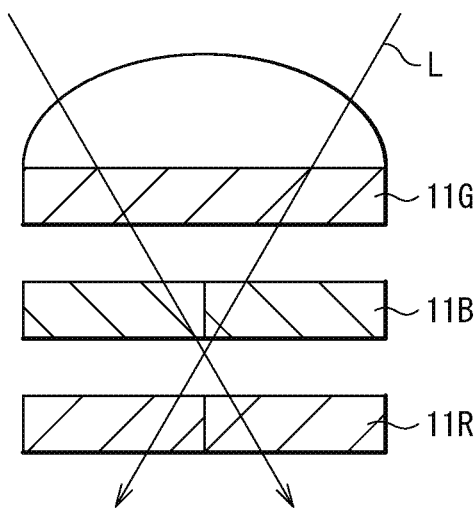

[FIG. 6]
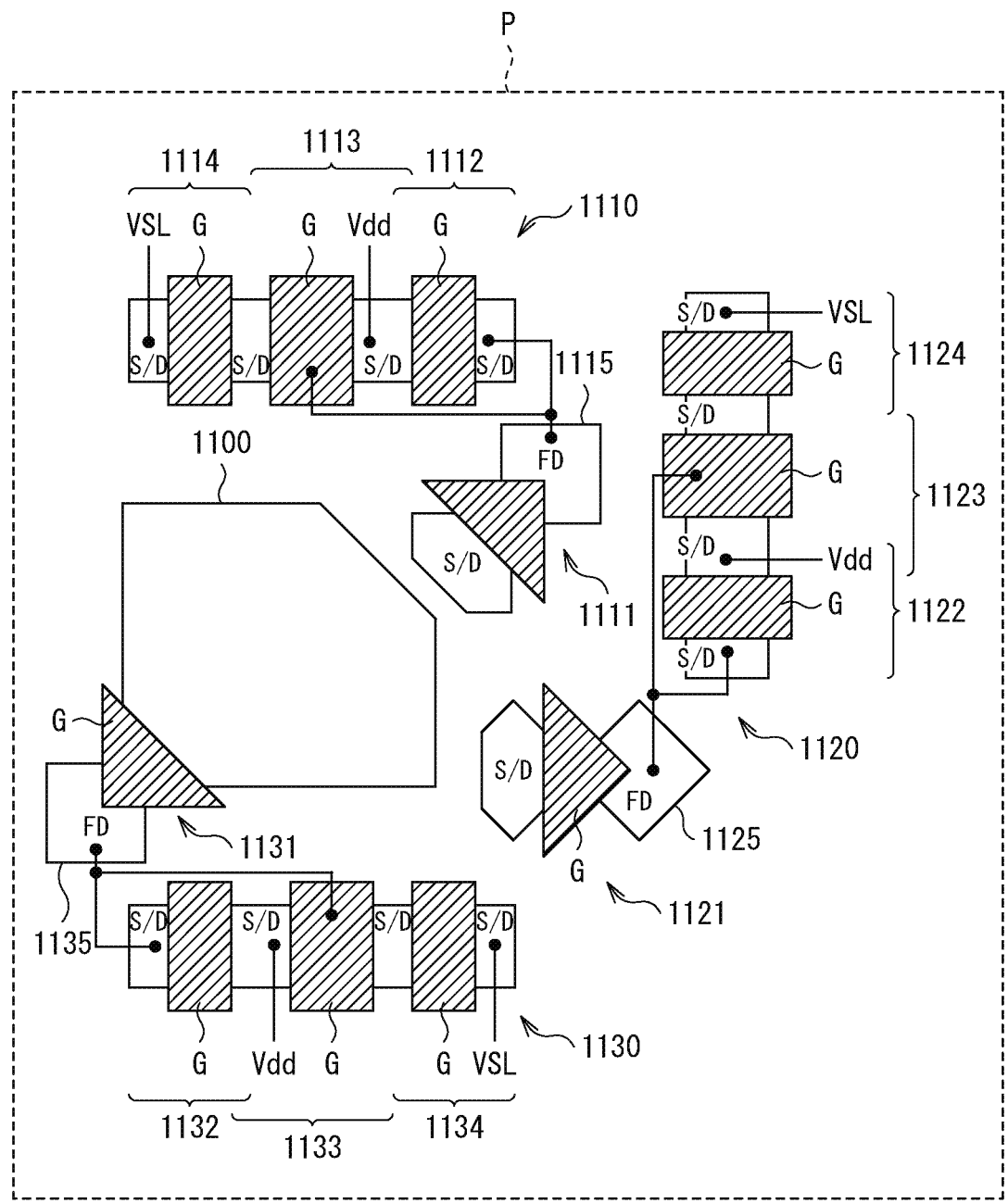

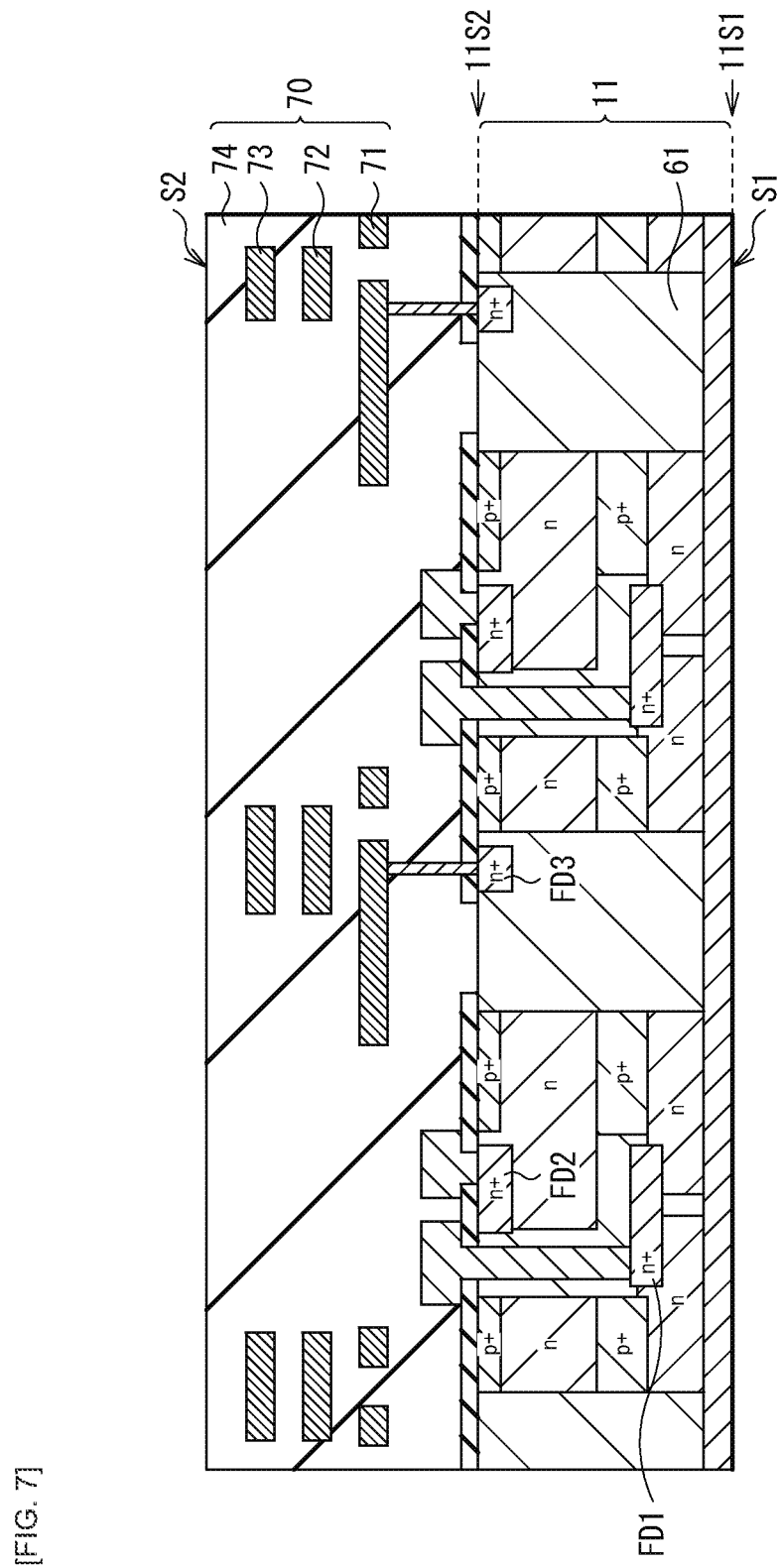
[FIG. 7]

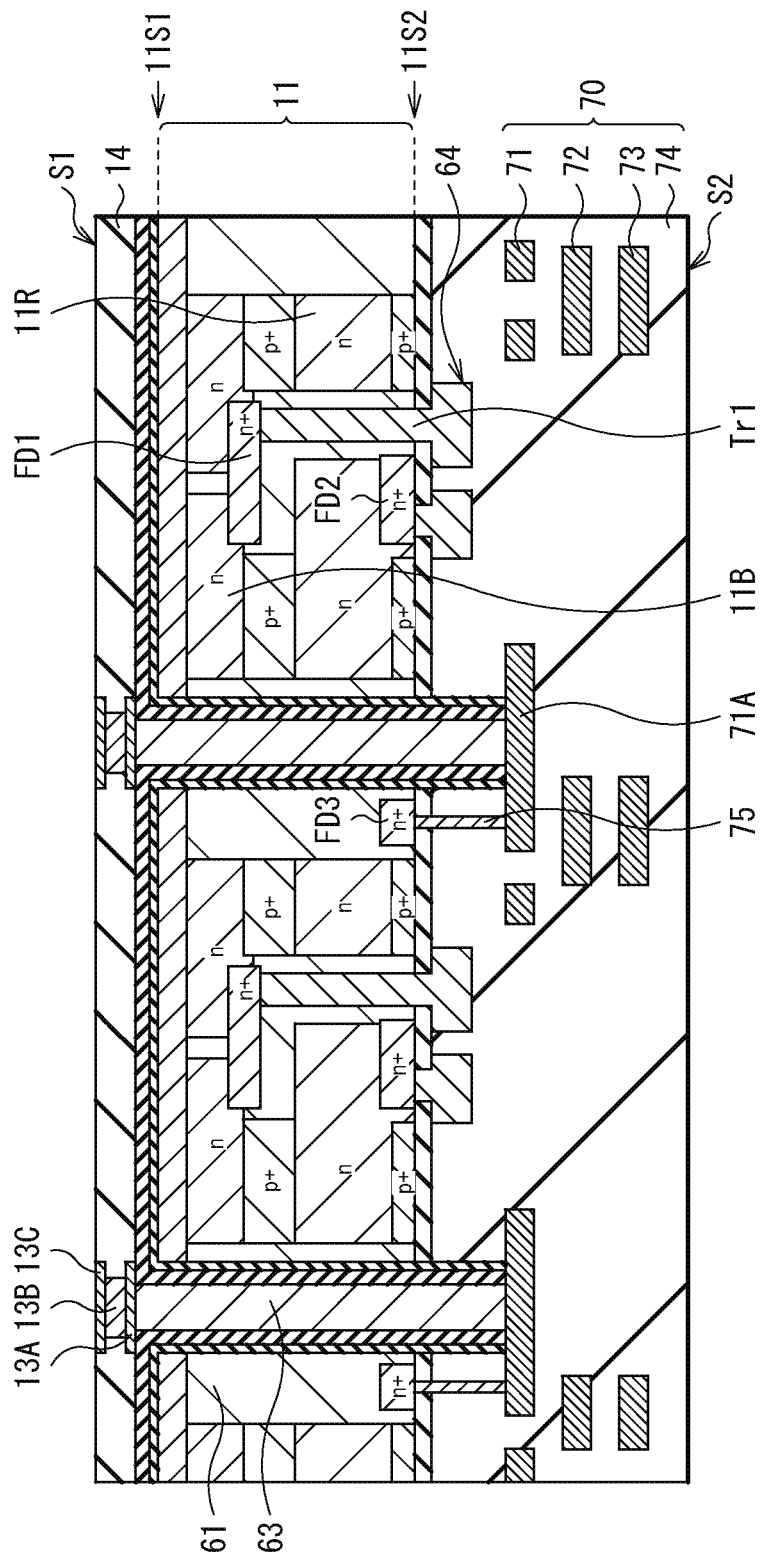
[FIG. 8]

[FIG. 9A]
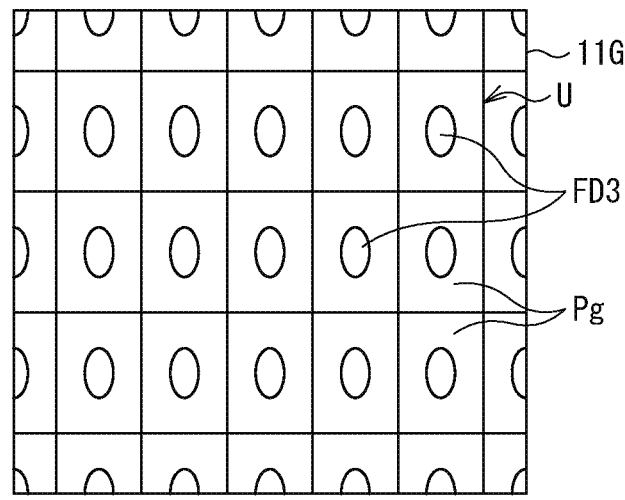
[FIG. 9B]
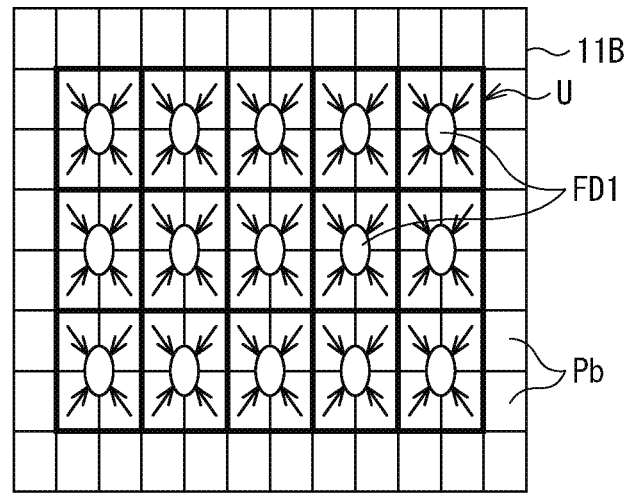
[FIG. 9C]
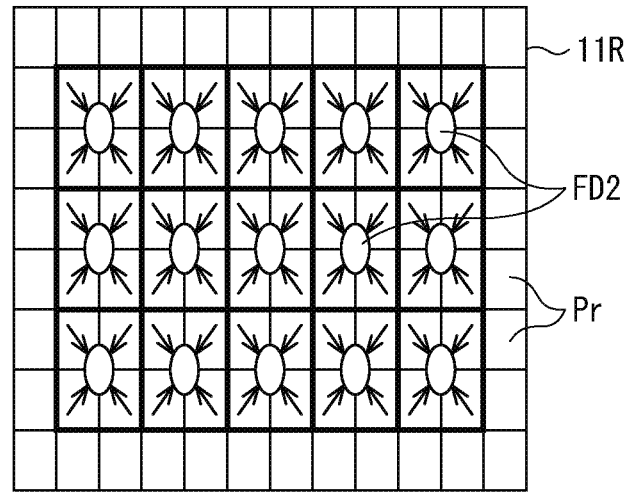

[FIG. 10]
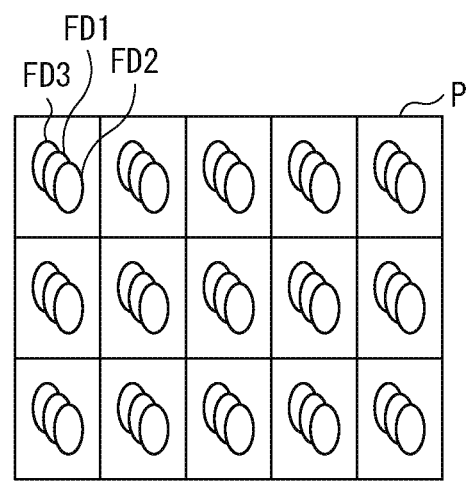

[FIG. 11A]
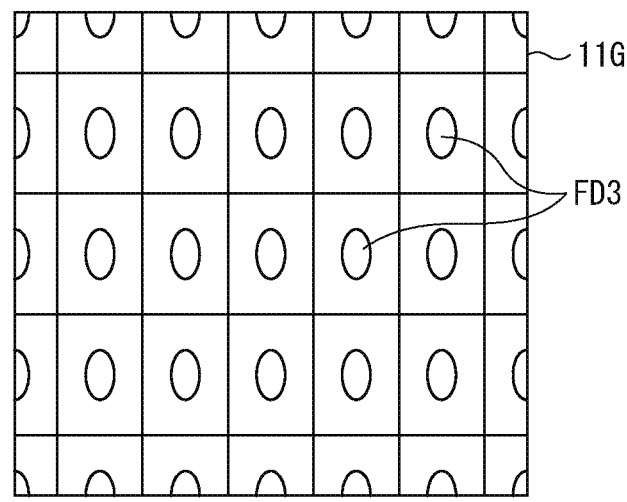
[FIG. 11B]
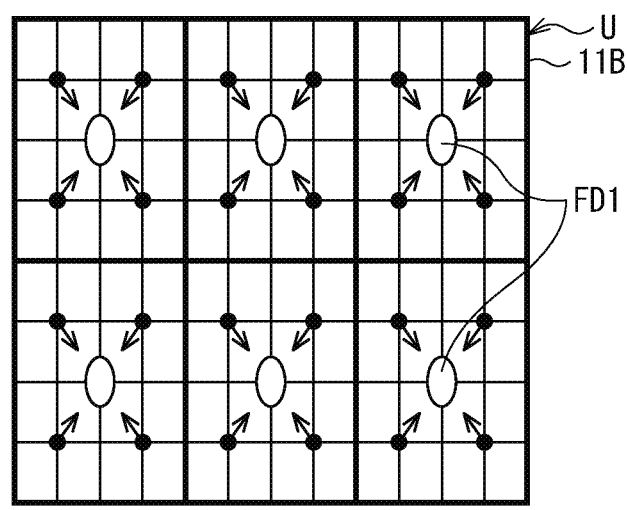
[FIG. 11C]
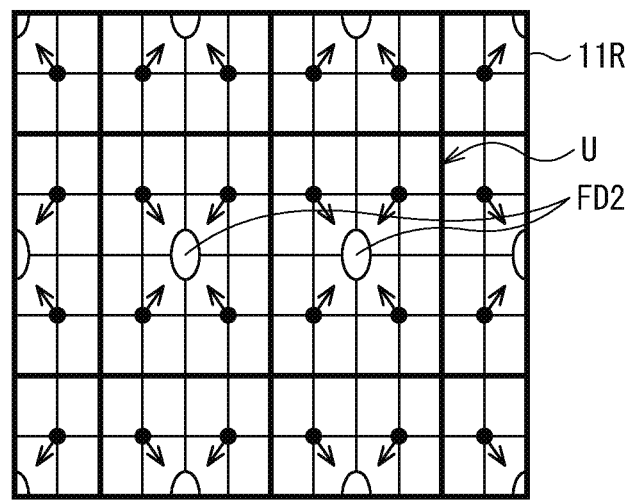

[FIG. 12]
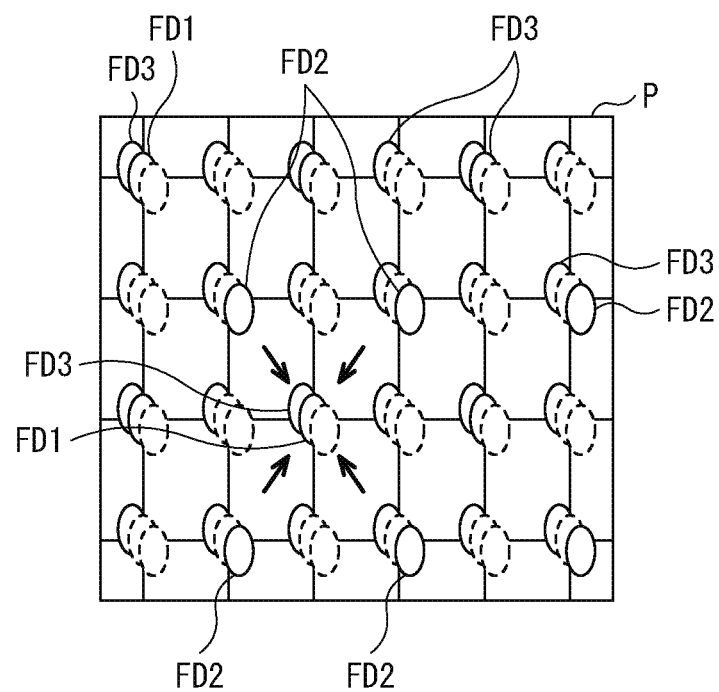

[FIG. 13A]
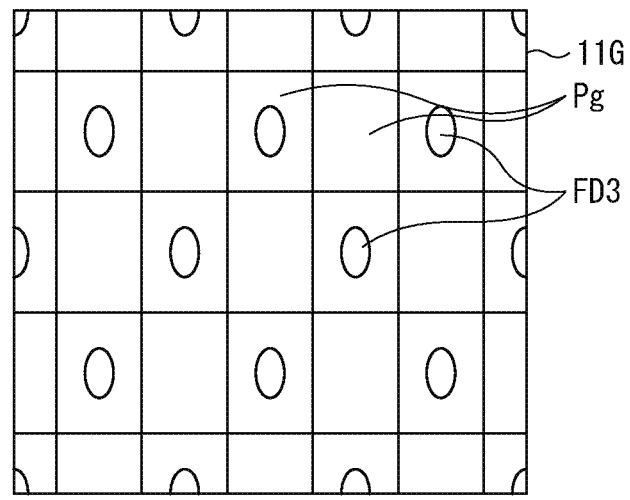
[FIG. 13B]
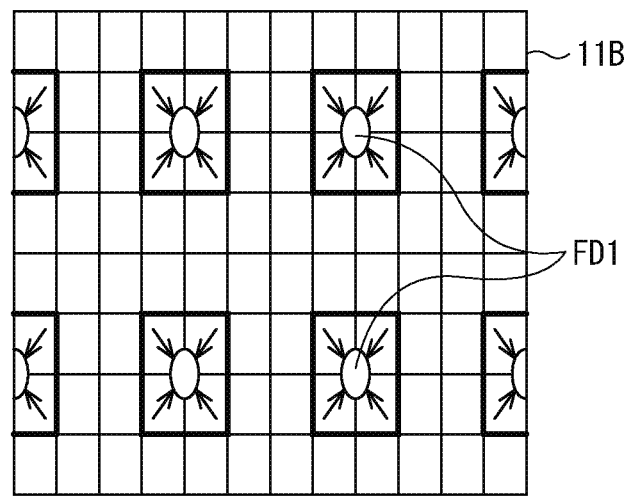
[FIG. 13C]
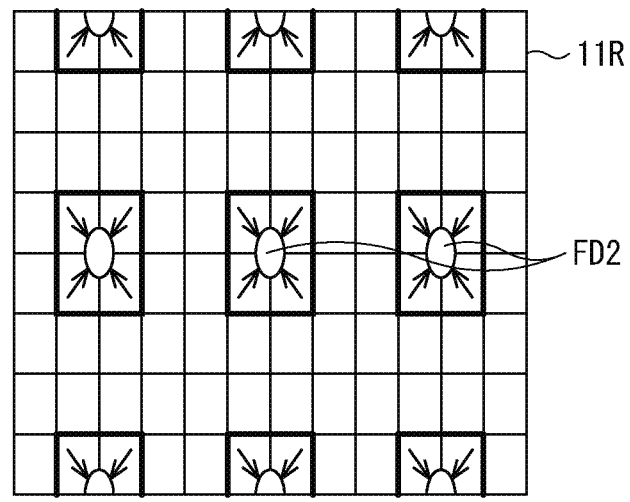

[FIG. 14]
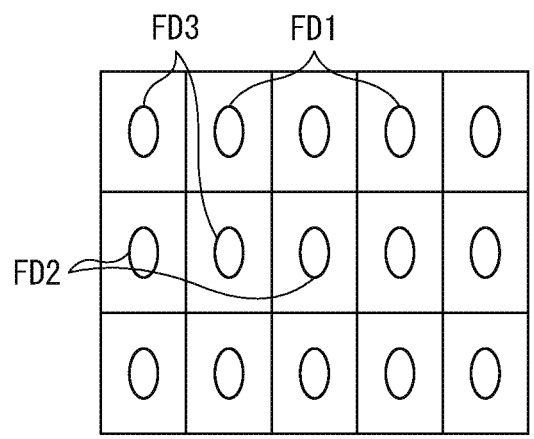
[FIG. 15]
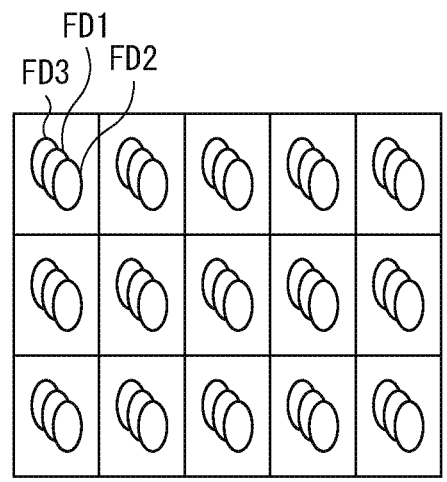

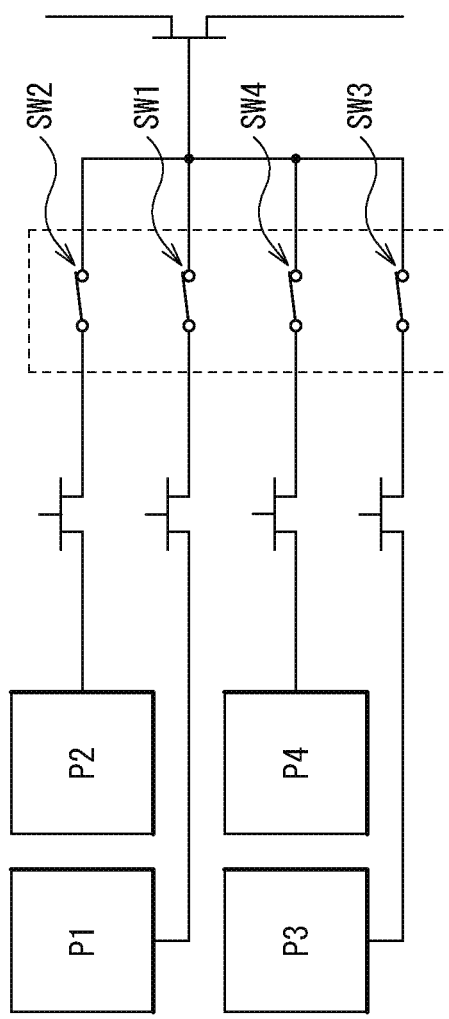
[FIG. 16]

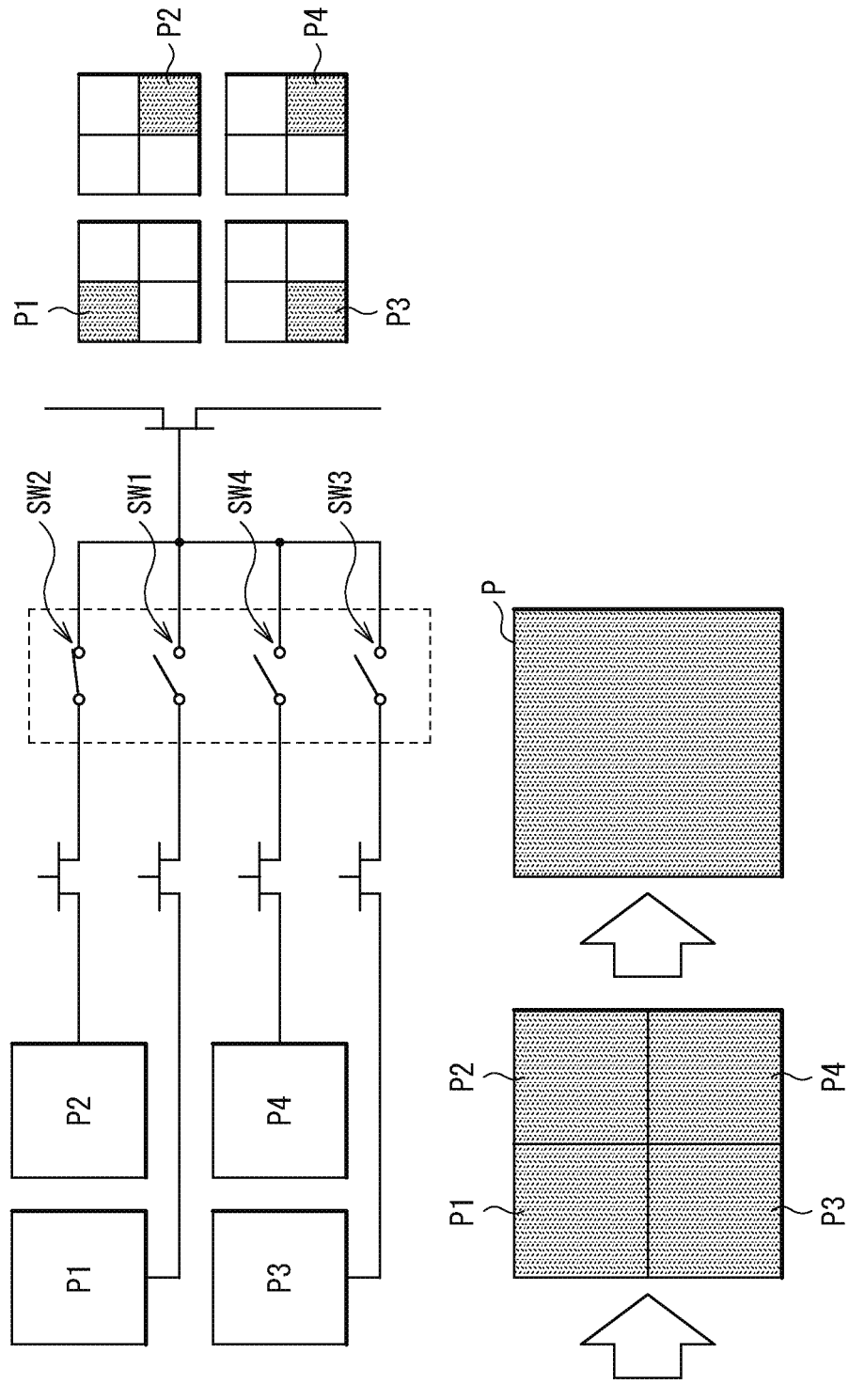
[FIG. 17]

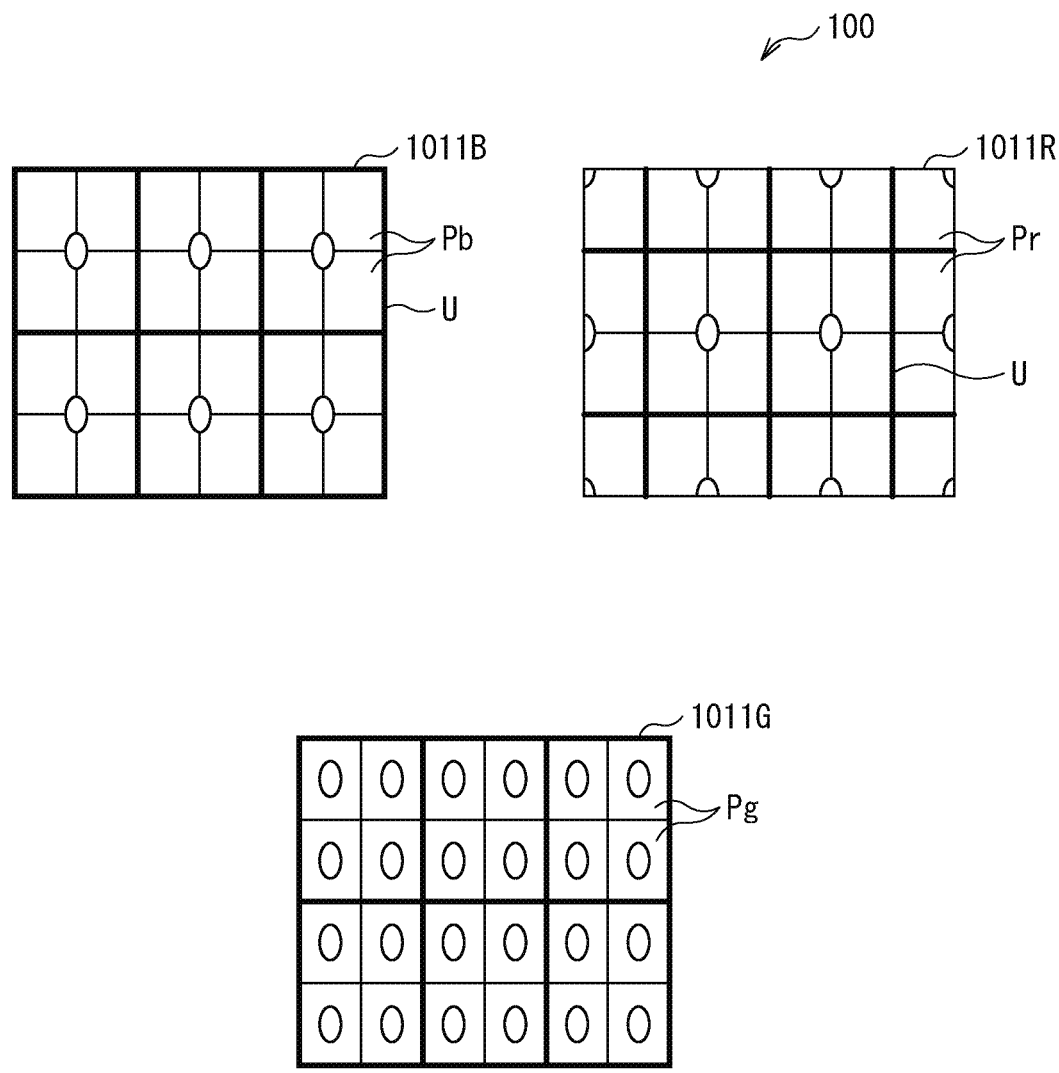

[FIG. 18B]
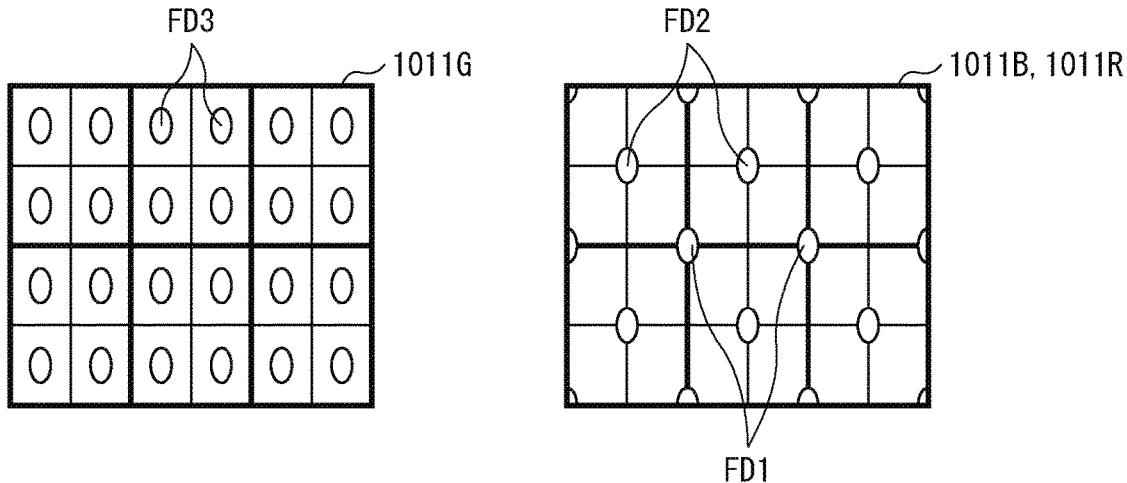
[FIG. 18C]
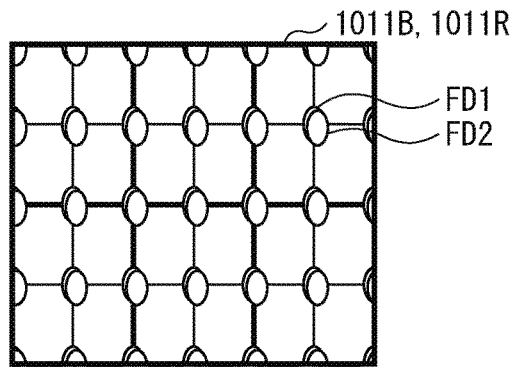
[FIG. 18D]
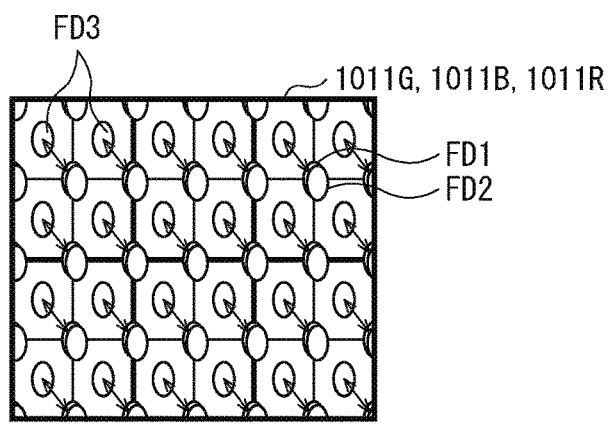

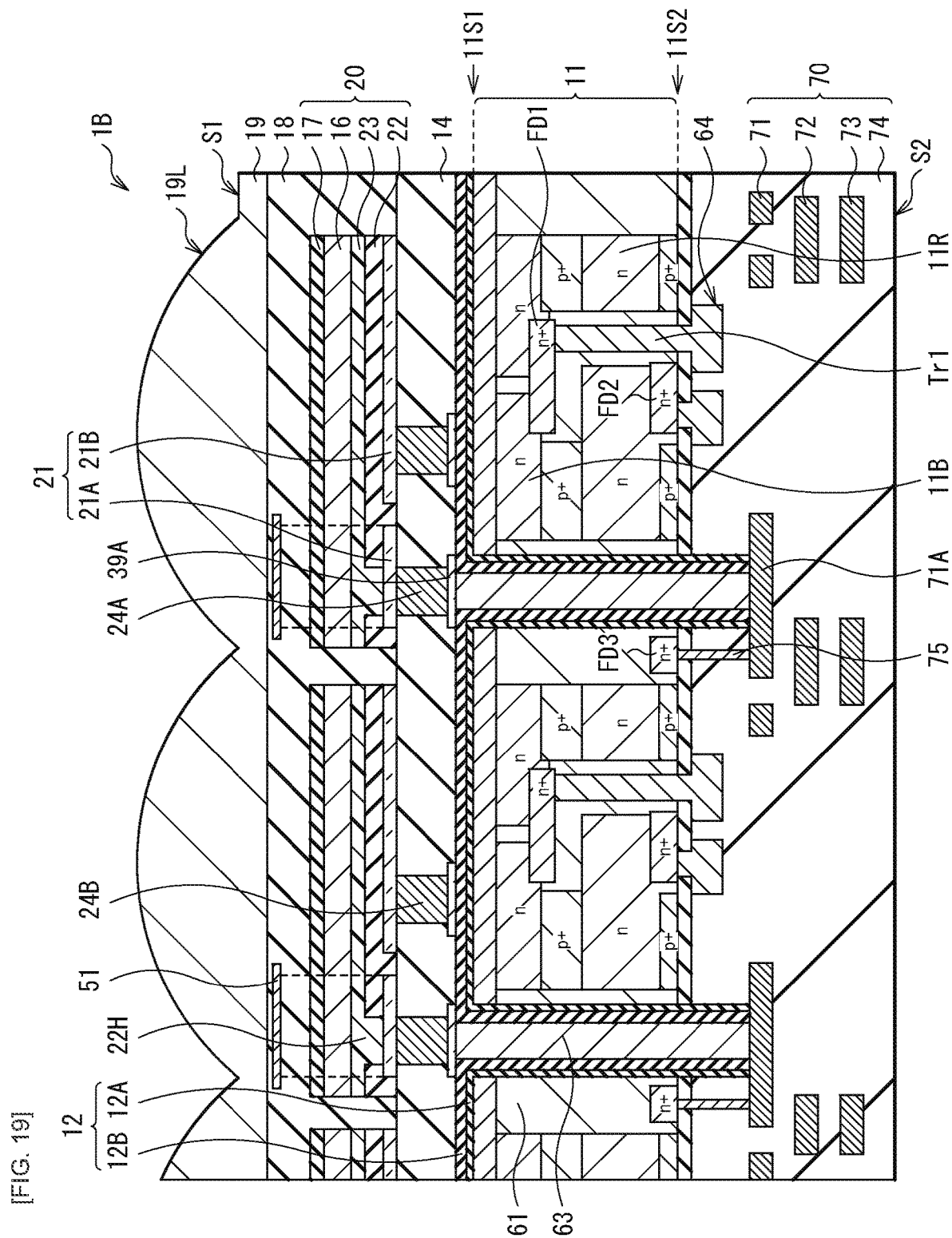

[FIG. 20]
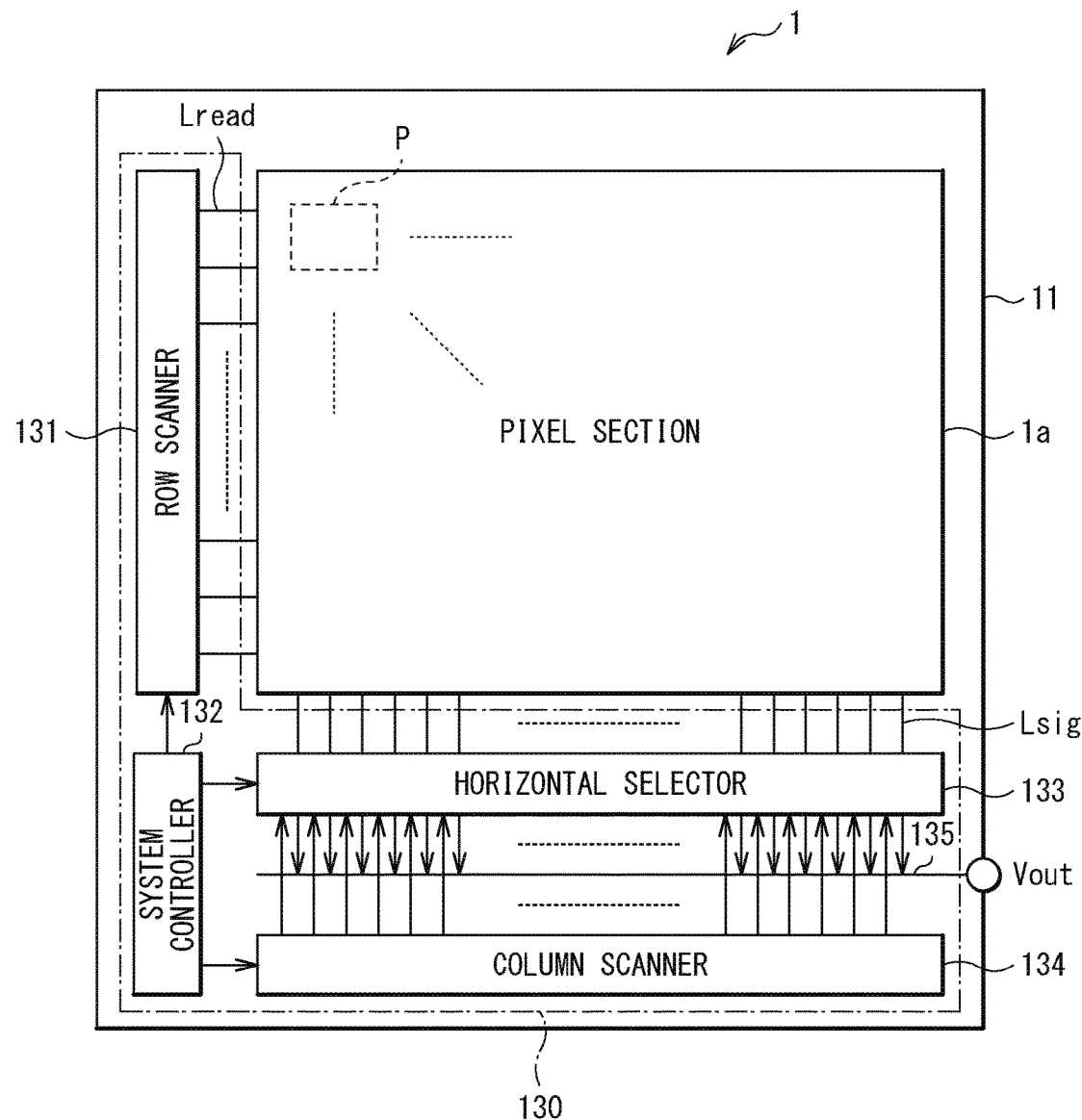

[FIG. 21]
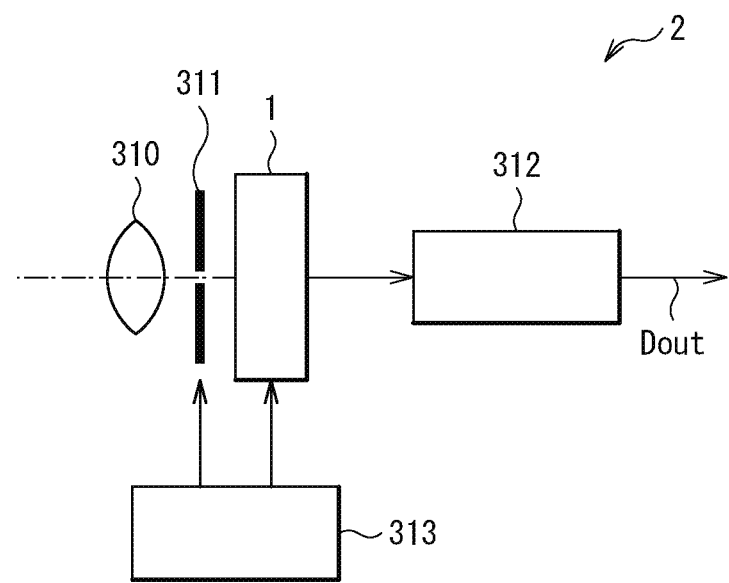

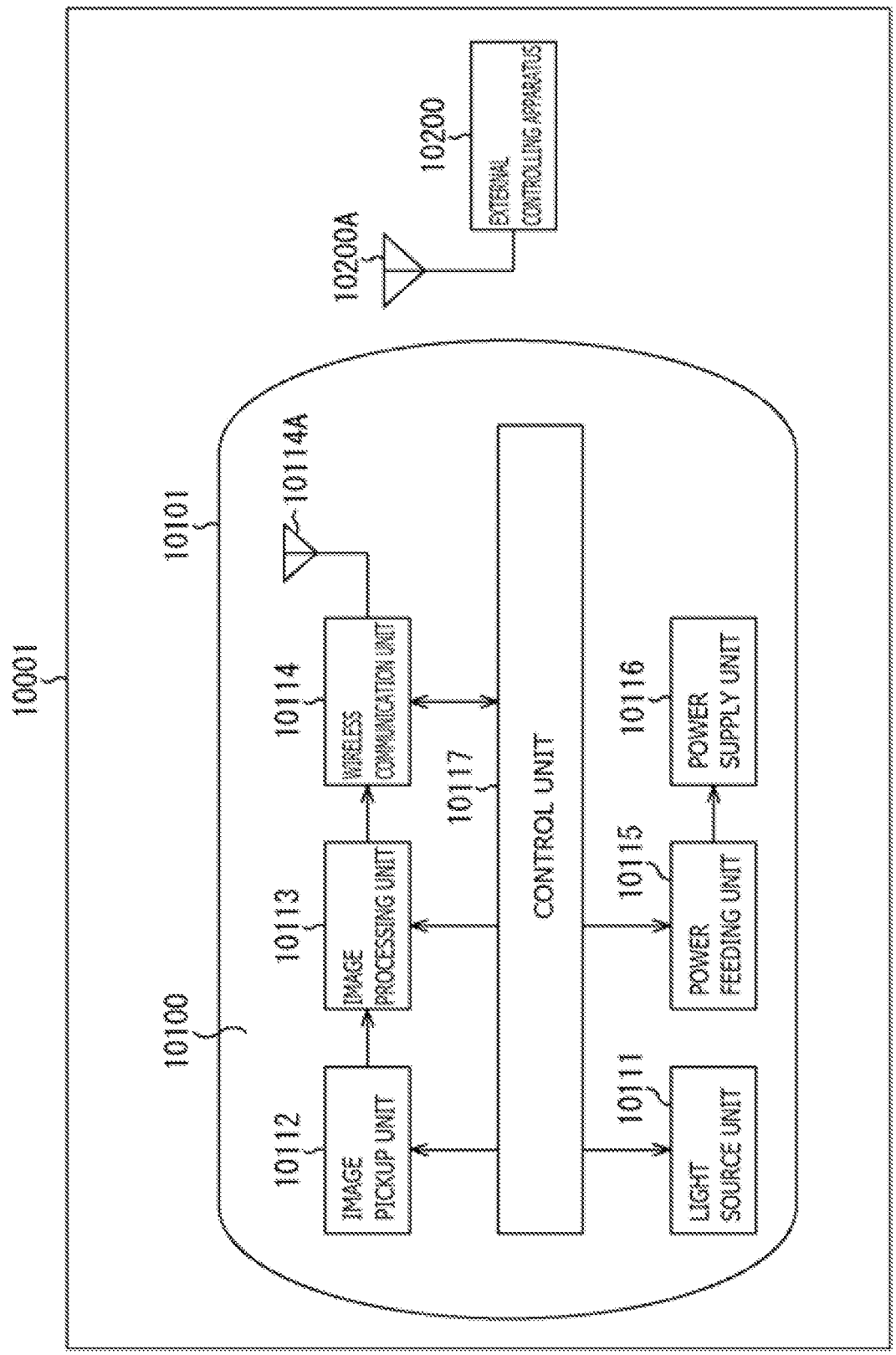
[FIG. 22]

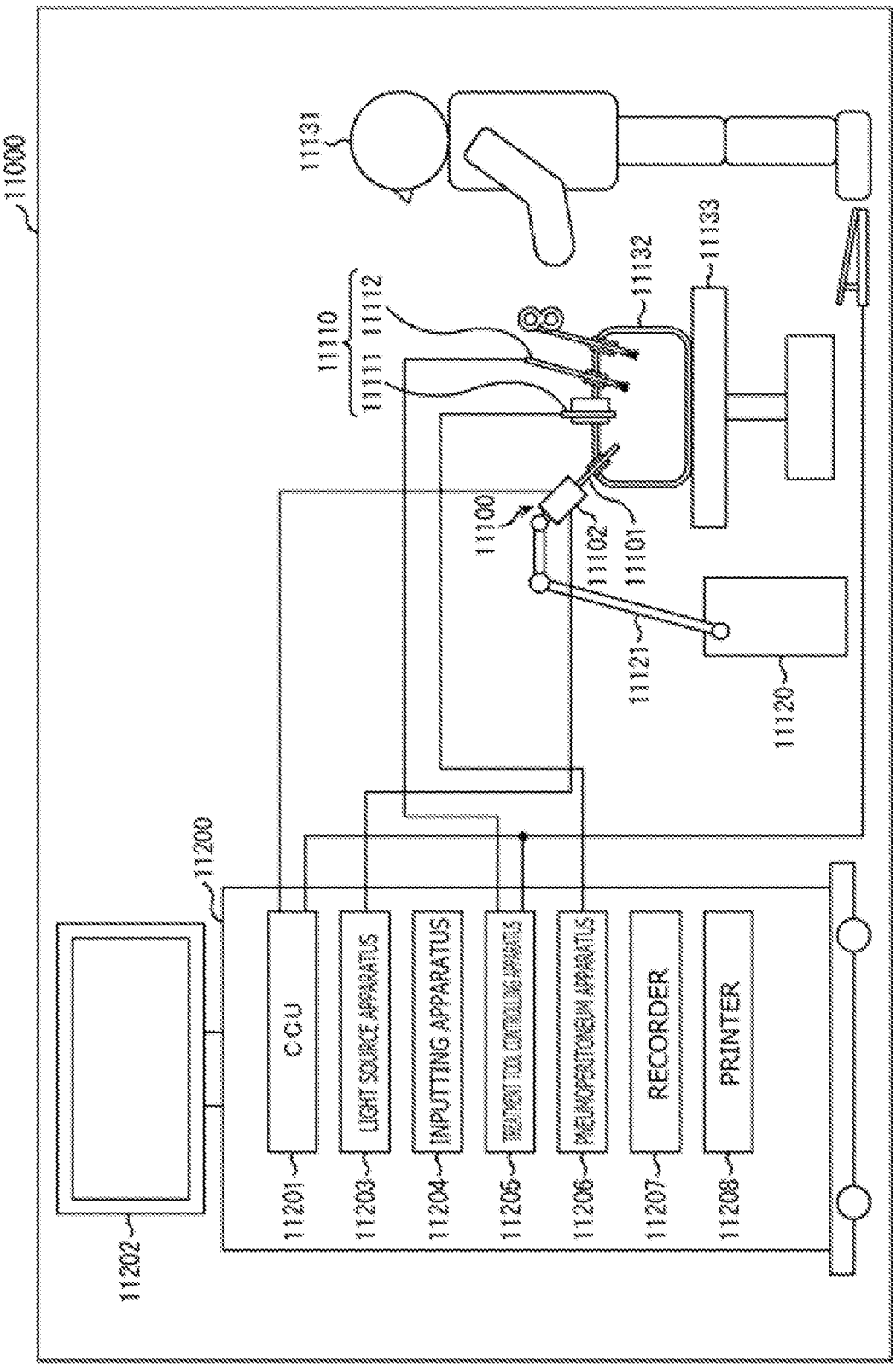
[FIG. 23]

[FIG. 24]
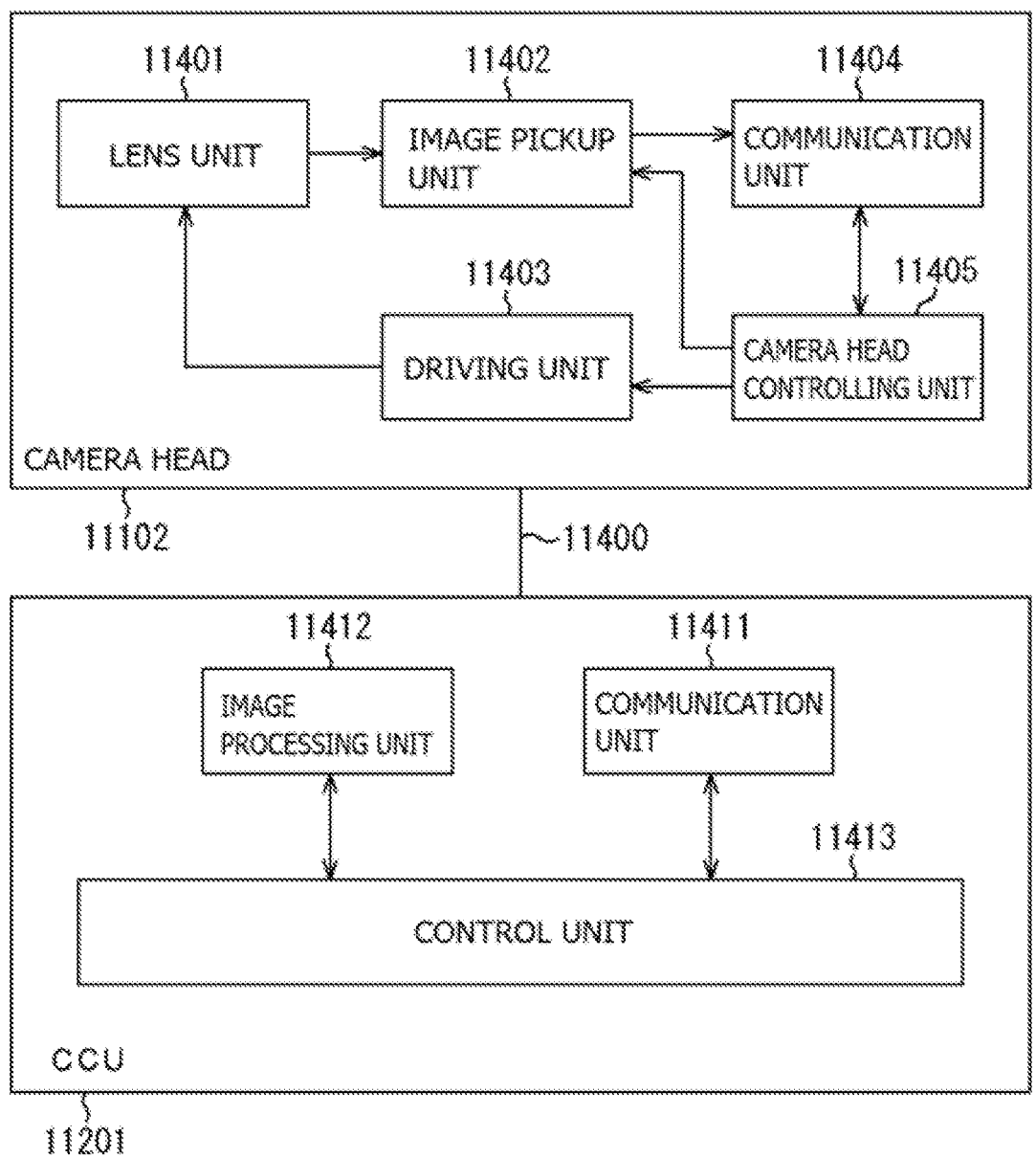

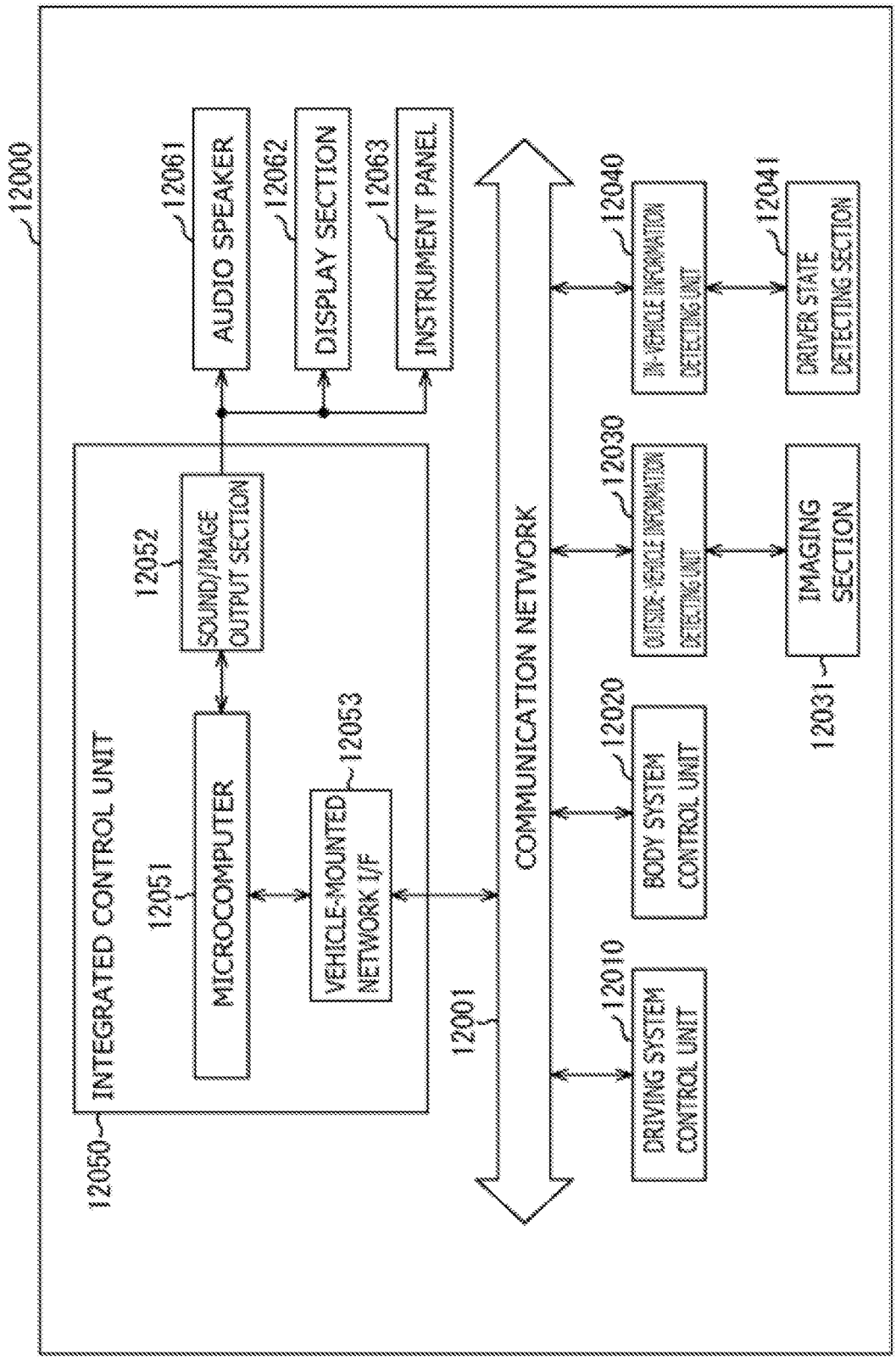

[FIG. 26]
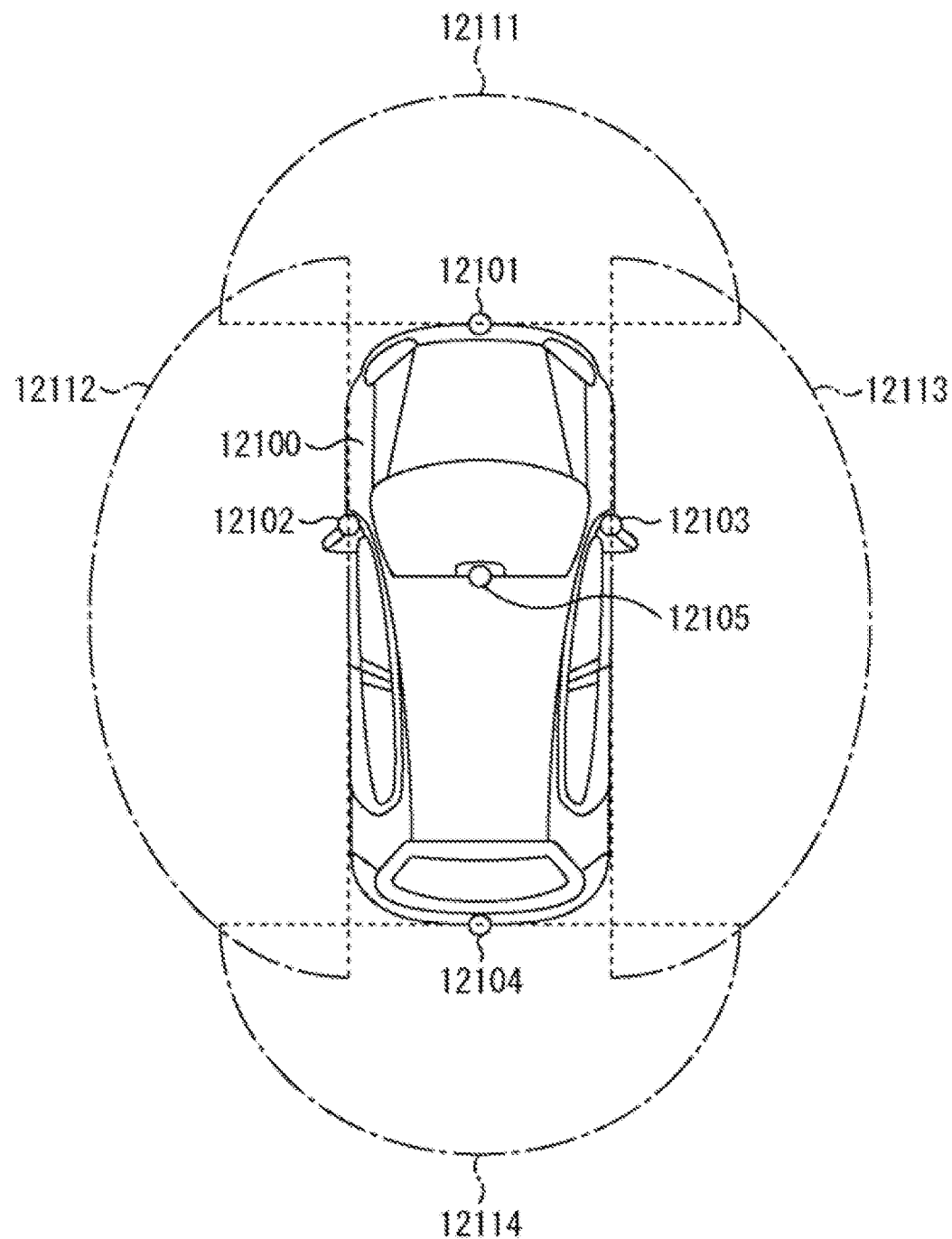

IMAGING ELEMENT, ELECTRONIC APPARATUS, AND METHOD OF DRIVING IMAGING ELEMENT

CROSS REFERENCE TO RELATED APPLICATIONS

This application is a U.S. National Phase of International Patent Application No. PCT/JP2019/017430 filed on Apr. 24, 2019, which claims priority benefit of Japanese Patent Application No. JP 2018-096530 filed in the Japan Patent Office on May 18, 2018. Each of the above-referenced applications is hereby incorporated herein by reference in its entirety.

TECHNICAL FIELD

The present disclosure relates, for example, to an imaging element in which a plurality of photoelectric conversion sections are stacked in a vertical direction, an electronic apparatus, and a method of driving the imaging element.

BACKGROUND ART

In recent years, there has been progress in reduction of a pixel size in a solid-state imaging device such as a CCD (Charge Coupled Device) image sensor or a CMOS (Complementary Metal Oxide Semiconductor) image sensor. This leads to a decrease in the number of photons that enter a unit pixel, thus leading to lowered sensitivity as well as a lowered S/N ratio. Further, in a case of using a color filter in which primary color filters of red, green, and blue are two-dimensionally arrayed for colorization, light beams of green and blue are absorbed by the color filter in a red pixel, for example, thus leading to lowered sensitivity. Furthermore, interpolation processing is performed between pixels upon generation of each color signal, thus causing occurrence of a so-called false color.

Thus, for example, PTL 1 discloses a so-called vertical spectroscopic solid-state imaging device in which an organic photoelectric conversion section including an organic photoelectric conversion film and two inorganic photoelectric conversion sections each having a p-n junction in a semiconductor substrate are stacked. In such a solid-state imaging device, signals of B/G/R are separately taken out from one pixel, thereby achieving an enhancement in the sensitivity.

CITATION LIST

Patent Literature

PTL 1: Japanese Unexamined Patent Application Publication No. 2011-29337

SUMMARY OF THE INVENTION

Incidentally, the vertical spectroscopic imaging device as described above is desired to achieve both resolution and granular feeling.

It is desirable to provide an imaging element that makes it possible to achieve an enhancement in resolution and an improvement in granular feeling, an electronic apparatus including the imaging element, and a method of driving the imaging element.

An imaging element according to an embodiment of the present disclosure includes a first photoelectric conversion section and a second photoelectric conversion section that are stacked in order from light incident side and that selectively detect and photoelectrically convert light beams of different wavelength bands, and the second photoelectric conversion section is disposed at an interval narrower than a pixel pitch of the first photoelectric conversion section.

An electronic apparatus according to an embodiment of the present disclosure includes a plurality of imaging elements for respective pixels, and includes, as each of the imaging elements, the above-described imaging element according to an embodiment of the present disclosure.

In an imaging element including a first photoelectric conversion section and a second photoelectric conversion section that are stacked in order from light incident side and selectively detect and photoelectrically convert light beams of different wavelength bands, in which the second photoelectric conversion section is disposed at an interval narrower than a pixel pitch of the first photoelectric conversion section, a method of driving the imaging element according to an embodiment of the present disclosure includes acquiring a color signal of first light using one pixel of the first photoelectric conversion section, and acquiring a color signal of second light of a wavelength band different from the first light by addition in a plurality of the second photoelectric conversion sections.

In the imaging element, the electronic apparatus, and the method of manufacturing the imaging element according to respective embodiments of the present disclosure, the first photoelectric conversion section and the second photoelectric conversion section that selectively detect and photoelectrically convert light beams of different wavelength bands are stacked in order from light incident side, and the pixel pitch of the second photoelectric conversion section constitutes an interval narrower than the pixel pitch of the first photoelectric conversion section. This allows for acquisition of color signals from the respective photoelectric conversion sections with no phase shift in the high-sensitivity mode, for example.

According to the imaging element, the electronic apparatus, and the method of manufacturing the imaging element of the respective embodiments of the present disclosure, in the first photoelectric conversion section and the second photoelectric conversion section that selectively detect and photoelectrically convert light beams of different wavelength bands, the pixel pitch of the second photoelectric conversion section is disposed at an interval narrower than the first photoelectric conversion section arranged on the light incident side. This makes it possible to acquire the color signals from the respective photoelectric conversion sections with no phase shift in the high-sensitivity mode, for example. Thus, it is possible to achieve an enhancement in resolution and an improvement in granular feeling.

It is to be noted that the effects described here are not necessarily limitative, and may be any of the effects described in the present disclosure.

BRIEF DESCRIPTION OF THE DRAWINGS

FIG. 1 is a perspective view illustrating a configuration of a main part of an imaging element according to an embodiment of the present disclosure.

FIG. 2 is a schematic plan view illustrating a configuration of an inorganic photoelectric conversion section with respect to an organic photoelectric conversion section of the imaging element illustrated in FIG. 1.

FIG. 3 is a schematic cross-sectional view of an example of a specific configuration of the imaging element illustrated in FIG. 1.

FIG. 4A is a schematic plan view of a relationship between an on-chip lens and the organic photoelectric conversion section of the imaging element illustrated in FIG. 3.

FIG. 4B is a schematic plan view of a relationship between the on-chip lens and the inorganic photoelectric conversion section of the imaging element illustrated in FIG. 3.

FIG. 5A is a schematic cross-sectional view of light (incident light) that enters the organic photoelectric conversion section via the on-chip lens.

FIG. 5B is a schematic cross-sectional view of light (incident light) that enters the inorganic photoelectric conversion section that acquires a blue signal via the on-chip lens.

FIG. 5C is a schematic cross-sectional view of light (incident light) that enters the inorganic photoelectric conversion section that acquires a red signal via the on-chip lens.

FIG. 6 is a schematic plan view of an example of a configuration of a unit pixel of the imaging element illustrated in FIG. 3.

FIG. 7 is a schematic cross-sectional view of an example of a manufacturing process of the imaging element illustrated in FIG. 3.

FIG. 8 is a schematic cross-sectional view of a process subsequent to FIG. 7.

FIG. 9A is a schematic plan view for describing a method of driving a green pixel in a high-resolution mode.

FIG. 9B is a schematic plan view for describing a method of driving a red pixel in the high-resolution mode.

FIG. 9C is a schematic plan view for describing a method of driving a blue pixel in the high-resolution mode.

FIG. 10 is a schematic plan view for describing development processing in the high-resolution mode.

FIG. 11A is a schematic plan view for describing a method of driving the green pixel in a high-sensitivity mode.

FIG. 11B is a schematic plan view for describing a method of driving the red pixel in the high-sensitivity mode.

FIG. 11C is a schematic plan view for describing a method of driving the blue pixel in the high-sensitivity mode.

FIG. 12 is a schematic plan view for describing development processing in the high-resolution mode.

FIG. 13A is a schematic plan view for describing a method of driving the green pixel in a high-speed mode.

FIG. 13B is a schematic plan view for describing a method of driving the red pixel in the high-speed mode.

FIG. 13C is a schematic plan view for describing a method of driving the blue pixel in the high-speed mode.

FIG. 14 is a schematic plan view for describing thinning processing in the high-speed mode.

FIG. 15 is a schematic plan view for describing development processing in the high-speed mode.

FIG. 16 describes FD addition.

FIG. 17 describes digital addition.

FIG. 18A is a schematic plan view for describing a high-sensitivity mode in a typical imaging element.

FIG. 18B is a schematic plan view for describing a high-sensitivity mode in the typical imaging element subsequent to FIG. 18A.

FIG. 18C is a schematic plan view for describing a high-sensitivity mode in the typical imaging element subsequent to FIG. 18B.

FIG. 18D is a schematic plan view for describing a high-sensitivity mode in the typical imaging element subsequent to FIG. 18C.

FIG. 19 is a schematic cross-sectional view of an example of a specific configuration of an imaging element according to a modification example of the present disclosure.

FIG. 20 is a block diagram illustrating an overall configuration of the imaging element illustrated in FIG. 1.

FIG. 21 is a functional block diagram illustrating an example of an electronic apparatus (camera) using the imaging element illustrated in FIG. 20.

FIG. 22 is a block diagram depicting an example of a schematic configuration of an in-vivo information acquisition system.

FIG. 23 is a view depicting an example of a schematic configuration of an endoscopic surgery system.

FIG. 24 is a block diagram depicting an example of a functional configuration of a camera head and a camera control unit (CCU).

FIG. 25 is a block diagram depicting an example of schematic configuration of a vehicle control system.

FIG. 26 is a diagram of assistance in explaining an example of installation positions of an outside-vehicle information detecting section and an imaging section.

MODES FOR CARRYING OUT THE INVENTION

In the following, description is given of embodiments of the present disclosure in detail with reference to the drawings. The following description is merely a specific example of the present disclosure, and the present disclosure should not be limited to the following aspects. Moreover, the present disclosure is not limited to arrangements, dimensions, dimensional ratios, and the like of each component illustrated in the drawings. It is to be noted that the description is given in the following order.

1. Embodiment (An example of an imaging element in which four pixels of an inorganic photoelectric conversion section are arranged with respect to one pixel of an organic photoelectric conversion section)
   1-1. Configuration of Imaging Element
   1-2. Method of Manufacturing Imaging Element
   1-3. Method of Driving Imaging Element
   1-4. Workings and Effects
2. Modification Example
3. Application Examples 1. Embodiment FIG. 1 is a schematic perspective view of a configuration of a main part (an organic photoelectric conversion section 11G and inorganic photoelectric conversion sections 11B and 11R) of an imaging element (an imaging element 1) of an embodiment of the present disclosure. FIG. 2 is a schematic plan view of a configuration of the inorganic photoelectric conversion sections 11B and 11R with respect to the organic photoelectric conversion section 11G of the imaging element 1 illustrated in FIG. 1. FIG. 3 schematically illustrates an example of a specific cross-sectional configuration of the imaging element 1 illustrated in FIG. 1. The imaging element 1 configures, for example, a CCD (Charge Coupled Device) image sensor or a CMOS (Complementary Metal Oxide Semiconductor) image sensor, etc. of a backside illumination type (backside light receiving type) (see FIG. 20). The imaging element 1 is of a so-called vertical spectroscopic type in which one organic photoelectric conversion section 11G and two inorganic photoelectric conversion sections 11B and 11R that selectively detect and perform photoelectric conversion of light beams of different wavelength bands are stacked in a vertical direction.

(1-1. Configuration of Imaging Element)

In the imaging element 1 of the present embodiment, the organic photoelectric conversion section 11G (first photoelectric conversion section), the inorganic photoelectric conversion section 11B (third photoelectric conversion section), and the inorganic photoelectric conversion section 11R (second photoelectric conversion section) are stacked in this order from light incident side, and the inorganic photoelectric conversion sections 11B and 11R are each disposed at a pixel pitch (w) narrower than a pixel pitch (W) of the organic photoelectric conversion section 11G with respect to one pixel of the organic photoelectric conversion section 11G. Specifically, in the imaging element 1, for example, four (2×2) pixels of the inorganic photoelectric conversion sections 11B and 11R are each arranged with respect to one pixel of the organic photoelectric conversion section 11G. That is, the inorganic photoelectric conversion sections 11B and 11R each have the pixel pitch (w) which is, for example, ½ (w=½W) with respect to the pixel pitch (W) of the organic photoelectric conversion section 11G, and are each ¼ in terms of area.

The organic photoelectric conversion section 11G and the inorganic photoelectric conversion sections 11B and 11R selectively detect and perform photoelectric conversion of light beams of different wavelength bands. Specifically, the organic photoelectric conversion section 11G acquires a color signal of green (G). The inorganic photoelectric conversion sections 11B and 11R acquire color signals of blue (B) and red (R), respectively, due to differences in absorption coefficients. This enables the imaging element 1 to acquire a plurality of types of color signals in one pixel without using a color filter.

It is to be noted that description is given, in the present embodiment, of a case of reading holes as signal charges from a pair of electrons and holes generated by photoelectric conversion (a case of adopting a p-type semiconductor region as a photoelectric conversion layer). In addition, in the diagram, "+(plus)" attached to "p" and "n" indicates that p-type or n-type impurity concentration is high.

The organic photoelectric conversion section 11G is provided on side of a back surface (a first surface 11S1) of a semiconductor substrate 11. The inorganic photoelectric conversion sections 11B and 11R are each formed to be embedded in the semiconductor substrate 11, and are stacked in a thickness direction of the semiconductor substrate 11.

The semiconductor substrate 11 is configured by, for example, an n-type silicon (Si) substrate, and includes a p-well 61 in a predetermined region. A second surface (front surface of the semiconductor substrate 11) 11S2 of the p-well 61 is provided with, for example, floating diffusions (floating diffusion layers) FD2 and FD3. Other than those, various transistors Tr (e.g., a TR group 1110 described later) are provided (e.g., see FIGS. 4A and 4B). Further, the second surface 11S2 of the semiconductor substrate 11 is provided with a multilayer wiring layer 70. The multilayer wiring layer 70 has a configuration in which, for example, wiring layers 71, 72, and 73 are stacked in an insulating layer 74. In addition, a peripheral part of the semiconductor substrate 11 is provided with a peripheral circuit (not illustrated) including a logic circuit or the like.

It is to be noted that, in FIG. 3, side of the first surface 11S1 of the semiconductor substrate 11 is denoted by a light incident surface S1, and side of the second surface 11S2 thereof is denoted by a wiring layer side S2.

The inorganic photoelectric conversion sections 11B and 11R are each configured by, for example, a PIN (Positive Intrinsic Negative) type photodiode, and each have a p-n junction in a predetermined region of the semiconductor substrate 11. The inorganic photoelectric conversion sections 11B and 11R enable light to be dispersed in the vertical direction by utilizing different wavelength bands to be absorbed depending on incidence depth of light in the silicon substrate.

The inorganic photoelectric conversion section 11B selectively detects blue light and accumulates signal charges corresponding to a blue color; the inorganic photoelectric conversion section 11B is installed at a depth at which the blue light is able to be efficiently subjected to photoelectric conversion. The inorganic photoelectric conversion section 11R selectively detects red light and accumulates signal charges corresponding to red light; the inorganic photoelectric conversion section 11R is installed at a depth at which the red light is able to be efficiently subjected to photoelectric conversion. It is to be noted that blue (B) is a color corresponding to a wavelength band of 450 nm to 495 nm, for example, and red (R) is a color corresponding to a wavelength band of 620 nm to 750 nm, for example. It is sufficient for each of the inorganic photoelectric conversion sections 11B and 11R to be able to detect light of a portion or all of each wavelength band.

Specifically, as illustrated in FIG. 3, each of the inorganic photoelectric conversion section 11B and the inorganic photoelectric conversion section 11R includes, for example, a p+ region serving as a hole accumulation layer and an n region serving as an electron accumulation layer (having a p-n-p stacked structure). The p+ region of the inorganic photoelectric conversion section 11B bends along a vertical transistor (a vertical transistor Tr1), for example, and is coupled to the p+ region of the inorganic photoelectric conversion section 11R. In addition, as described above, in the inorganic photoelectric conversion sections 11B and 11R, four inorganic photoelectric conversion sections 11B and four inorganic photoelectric conversion sections 11R are each arranged in a 2×2 array with respect to one organic photoelectric conversion section 11G. In the inorganic photoelectric conversion sections 11B and 11R, for example, as illustrated in FIGS. 9B and 9C described later, one floating diffusion FD1 or FD2 is arranged for each 2×2 array, for example.

A portion of the floating diffusion FD1 is formed in the n region of the inorganic photoelectric conversion section 11B provided in the semiconductor substrate 11 to be thereby electrically coupled to the inorganic photoelectric conversion section 11B. For example, a gate wiring layer 64 that configures the vertical transistor Tr1 is electrically coupled to the floating diffusion FD1. The floating diffusion FD2 is provided, for example, to face the second surface 11S2 of the semiconductor substrate 11; a portion of the floating diffusion FD2 is formed in the n region of the inorganic photoelectric conversion section 11R provided in the semiconductor substrate 11 to be thereby electrically coupled to the inorganic photoelectric conversion section 11R.

Other than those, as described above, the second surface 11S2 of the semiconductor substrate 11 is provided with, for example, the floating diffusion FD3, and various transistors such as the vertical transistor Tr1 and the Tr group 1110 described later.

A lower contact 75 is configured by, for example, a doped silicon material such as PDAS (Phosphorus Doped Amorphous Silicon), or a metal material such as aluminum (Al), tungsten (W), titanium (Ti), cobalt (Co), hafnium (Hf), and tantalum (Ta).

The organic photoelectric conversion section 11G is provided on the side of the first surface 11S1 of the semiconductor substrate 11. The organic photoelectric conversion section 11G has a configuration in which, for example, a lower electrode 15, an organic photoelectric conversion layer 16, and an upper electrode 17 are stacked in this order from the side of the first surface S1 of the semiconductor substrate 11. The lower electrode 15 is formed separately for each unit pixel P, for example. The organic photoelectric conversion layer 16 and the upper electrode 17 are provided as successive layers common to a plurality of unit pixels P (e.g., a pixel section 1a of the imaging element 1 illustrated in FIGS. 18A, 18B, 18C, and 18D). The organic photoelectric conversion section 11G is an organic photoelectric conversion element that absorbs green light corresponding to a portion or all of a selective wavelength band (e.g., ranging from 450 nm to 650 nm) and generates electron-hole pairs.

Interlayer insulating layers 12 and 14 are stacked in this order, for example, from side of the semiconductor substrate 11 between the first surface 11S1 of the semiconductor substrate 11 and the lower electrode 15. The interlayer insulating layer 12 has a configuration in which, for example, a layer having a fixed charge (fixed charge layer) 12A and a dielectric layer 12B having an insulating property are stacked. A protective layer 18 is provided on the upper electrode 17. An on-chip lens layer 19, which configures an on-chip lens 19L and serves also as a planarization layer, is disposed above the protective layer 18.

A through electrode 63 is provided between the first surface 11S1 and the second surface 11S2 of the semiconductor substrate 11. The organic photoelectric conversion section 11G is coupled to each of the floating diffusion FD3 and a gate of an amplifier transistor AMP, which is not illustrated, via the through electrode 63. This makes it possible for the imaging element 1 to favorably transfer charges generated in the organic photoelectric conversion section 11G on the side of the first surface 11S1 of the semiconductor substrate 11 to the side of the second surface 11S2 of the semiconductor substrate 11 via the through electrode 63, and thus to enhance the characteristics.

The through electrode 63 is provided, for example, for each organic photoelectric conversion section 11G of the imaging element 1. The through electrode 63 functions as a connector between the organic photoelectric conversion section 11G and the floating diffusion FD3 as well as the gate of the amplifier transistor AMP, and serves as a transmission path for charges generated in the organic photoelectric conversion section 11G.

The lower end of the through electrode 63 is coupled to, for example, a coupling section 71A in the wiring layer 71, and the coupling section 71A and the gate of the amplifier transistor AMP are coupled to each other via, for example, a contact, which is not illustrated, having a configuration similar to that of the lower contact 75. The coupling section 71A and the floating diffusion FD3 are coupled to the lower electrode 15 via the lower contact 75. It is to be noted that, in FIG. 1, the through electrode 63 is illustrated to have a cylindrical shape, but this is not limitative; the through electrode 63 may have a tapered shape, for example.

Although not illustrated, a reset gate of a reset transistor RST is preferably arranged next to the floating diffusion FD3. This makes it possible to reset charges accumulated in the floating diffusion FD3 by the reset transistor RST.

In the imaging element 1, light incident on the organic photoelectric conversion section 11G from side of the upper electrode 17 is absorbed by the organic photoelectric conversion layer 16. Excitons thus generated move to an interface between an electron donor and an electron acceptor that constitute the organic photoelectric conversion layer 16, and undergo exciton separation, i.e., dissociate into electrons and holes. The charges (electrons and holes) generated here are transported to different electrodes by diffusion due to a difference in carrier concentrations or by an internal electric field due to a difference in work functions between an anode (here, the lower electrode 15) and a cathode (here, the upper electrode 17), and are detected as a photocurrent. In addition, application of an electric potential between the lower electrode 15 and the upper electrode 17 makes it possible to control directions in which electrons and holes are transported.

In the following, description is given of configurations, materials, and the like of the respective sections.

The organic photoelectric conversion section 11G includes the organic photoelectric conversion layer 16 including a p-type semiconductor and an n-type semiconductor and having a bulk hetero junction structure in a layer. The bulk hetero junction structure is a p/n junction plane formed by mixing a p-type semiconductor and an n-type semiconductor. The organic photoelectric conversion section 11G is an organic photoelectric conversion element that absorbs light corresponding to a portion or all of a selective wavelength band (e.g., ranging from 450 nm to 750 nm) and generates electron-hole pairs. As described above, the organic photoelectric conversion section 11G is configured by, for example, the lower electrode 15 and the upper electrode 17 that are disposed to be opposed to each other, and the organic photoelectric conversion layer 16 provided between the lower electrode 15 and the upper electrode 17.

The lower electrode 15 is provided in a region opposed to and covering light receiving surfaces of the four inorganic photoelectric conversion sections 11B and the four inorganic photoelectric conversion sections 11R, which are each arranged in 2×2, formed in the semiconductor substrate 11. The lower electrode 15 is configured by a metal oxide having light transmissivity. Examples of a metal atom that configures the metal oxide used as a material of the lower electrode 15 include tin (Sn), zinc (Zn), indium (In), silicon (Si), zirconium (Zr), aluminum (Al), gallium (Ga), tungsten (W), chromium (Cr), cobalt (Co), nickel (Ni), tantalum (Ta), niobium (Nb) and molybdenum (Mo). Examples of a metal oxide containing one or more of the above-mentioned metal atoms include ITO (indium tin oxide). However, as the constituent material of the lower electrode 15, there may be used, in addition to the ITO, tin oxide ($SnO_2$)-based material doped with a dopant or a zinc oxide-based material into which aluminum zinc oxide is doped with a dopant. Examples of the zinc oxide-based material include aluminum zinc oxide (AZO) doped with aluminum (Al) as a dopant, gallium zinc oxide (GZO) doped with gallium (Ga), and indium zinc oxide (IZO) doped with indium (In). In addition, other than those described above, CuI, $InSbO_4$, ZnMgO, $CuInO_2$, $MgIn_2O_4$, CdO, $ZnSnO_3$, or the like may be used.

The organic photoelectric conversion layer 16 converts optical energy into electric energy. The organic photoelectric conversion layer 16 includes, for example, two or more kinds of organic semiconductor materials (p-type semiconductor material or n-type semiconductor material) that function as a p-type semiconductor or an n-type semiconductor, respectively. The organic photoelectric conversion layer 16 includes, in the layer, a junction plane (p/n junction plane) between the p-type semiconductor material and the n-type semiconductor material. The p-type semiconductor functions relatively as an electron donor (donor), and the n-type semiconductor functions relatively as an electron acceptor (acceptor). The organic photoelectric conversion layer 16 provides a field in which excitons generated upon light absorption are separated into electrons and holes; specifically, excitons are separated into electrons and holes at an interface (p/n junction plane) between the electron donor and the electron acceptor.

The organic photoelectric conversion layer 16 may include, other than the p-type semiconductor material and the n-type semiconductor material, an organic semiconductor material, i.e., a so-called dye material that performs photoelectric conversion of light of a predetermined wavelength band, while transmitting light of another wavelength band. In a case of forming the organic photoelectric conversion layer 16 using three kinds of organic semiconductor materials of a p-type semiconductor material, an n-type semiconductor material, and a dye material, the p-type semiconductor material and the n-type semiconductor material are each preferably a material having light transmissivity in a visible region (e.g., 450 nm to 800 nm). The organic photoelectric conversion layer 16 has a thickness of, for example, 50 nm to 500 nm.

Examples of the organic semiconductor material that configures the organic photoelectric conversion layer 16 include quinacridone, chlorinated boron subphthalocyanine, pentacene, benzothienobenzothiophene, fullerene, and a derivative thereof. The organic photoelectric conversion layer 16 is configured by combining two or more kinds of the above-mentioned organic semiconductor materials. The above-mentioned organic semiconductor materials function as a p-type semiconductor or an n-type semiconductor depending on combinations thereof.

It is to be noted that there are no particular limitations on the organic semiconductor material that configures the organic photoelectric conversion layer 16. Other than the above-mentioned organic semiconductor material, for example, any one of naphthalene, anthracene, phenanthrene, tetracene, pyrene, perylene and fluoranthene, or a derivative thereof is suitably used. Alternatively, there may be used a polymer such as phenylenevinylene, fluorene, carbazole, indole, pyrene, pyrrole, picoline, thiophene, acetylene and diacetylene, and a derivative thereof. In addition, a condensed polycyclic aromatic compound and a chain compound in which an aromatic cyclic or heterocyclic compound is condensed, such as a metal complex dye, a cyanine-based dye, a merocyanine-based dye, a phenylxanthene-based dye, a triphenylmethane-based dye, a rhodacyanine-based dye, a xanthene-based dye, a macrocyclic azaannulene-based dye, an azulene-based dye, naphthoquinone, an anthraquinone-based dye, anthracene, and pyrene may be preferably used. Alternatively, two nitrogen-containing heterocyclic rings such as quinolines, benzothiazoles, and benzoxazoles each having a squarylium group and a croconic methine group as a linking chain, or a cyanine-like dye, etc., linked by the squarylium group and the croconic methine group may be preferably used. It is to be noted that, as the above-mentioned metal complex dye, a dithiol metal complex dye, a metal phthalocyanine dye, a metal porphyrin dye, or a ruthenium complex dye is preferred; however, this is not limitative.

The upper electrode 17 is configured by an electrically-conductive film having light transmissivity, similarly to the lower electrode 15. In the imaging element 1, the upper electrode 17 may be separated for each unit pixel P, or may be formed as a common electrode for each unit pixel P. The upper electrode 17 has a thickness of, for example, 10 nm to 200 nm.

It is to be noted that other layers may be provided between the organic photoelectric conversion layer 16 and the lower electrode 15 and between the organic photoelectric conversion layer 16 and the upper electrode 17. Specifically, for example, an underlying layer, a hole transport layer, an electron block layer, the organic photoelectric conversion layer 16, a hole block layer, a buffer layer, an electron transport layer, a work function adjusting layer, and the like may be stacked in order from side of the lower electrode 15.

The fixed charge layer 12A may be a film having a positive fixed charge or a film having a negative fixed charge. Examples of a material of the film having a negative fixed charge include hafnium oxide ($HfO_2$), aluminum oxide ($Al_2O_3$), zirconium oxide ($ZrO_2$), tantalum oxide ($Ta_2O_5$), and titanium oxide ($TiO_2$). In addition, as a material other than those mentioned above, there may be used lanthanum oxide, praseodymium oxide, cerium oxide, neodymium oxide, promethium oxide, samarium oxide, europium oxide, gadolinium oxide, terbium oxide, dysprosium oxide, holmium oxide, thulium oxide, ytterbium oxide, lutetium oxide, yttrium oxide, an aluminum nitride film, a hafnium oxynitride film, an aluminum oxynitride film, or the like.

The fixed charge layer 12A may have a configuration in which two or more kinds of films are stacked. This makes it possible to further enhance a function as the hole accumulation layer, for example, in a case of the film having a negative fixed charge.

A material of the dielectric layer 12B is not particularly limited, and the dielectric layer 12B is formed by, for example, a silicon oxide film, a TEOS film, a silicon nitride film, a silicon oxynitride film, or the like.

Pad sections 13A and 13C and an upper contact 13B are each configured by a doped silicon material such as PDAS (Phosphorus Doped Amorphous Silicon), or a metal material such as aluminum (Al), tungsten (W), titanium (Ti), cobalt (Co), hafnium (Hf), or tantalum (Ta), for example, similarly to the lower contact 75.

The interlayer insulating layer 14 is configured by a monolayer film of one of silicon oxide (SiO), silicon nitride (SiN), silicon oxynitride (SiON), and the like, for example, or alternatively is configured by a stacked film of two or more thereof.

The protective layer 18 is configured by a material having light transmissivity, and is configured by a monolayer film of one of silicon oxide, silicon nitride, silicon oxynitride, and the like, for example, or alternatively is configured by a stacked film of two or more thereof. The protective layer 18 has a thickness of, for example, 100 nm to 30000 nm.

The on-chip lens layer 19 is formed on the protective layer 18 to cover the entire surface thereof. A plurality of on-chip lenses (microlenses) 19L is provided on the front surface of the on-chip lens layer 19. The on-chip lens 19L condenses light incident from above on respective light receiving surfaces of the organic photoelectric conversion section 11G and the inorganic photoelectric conversion sections 11B and 11R.

In the imaging element 1, as described above, the four inorganic photoelectric conversion sections 11B (blue pixels Pb) arranged in 2×2 and the four inorganic photoelectric conversion sections 11R (red pixels Pr) arranged in 2×2 are disposed with respect to one organic photoelectric conversion section 11G (a green pixel Pg). Therefore, in the present embodiment, as illustrated in FIGS. 4A and 4B, one organic photoelectric conversion section 11G (one green pixel Pg), four inorganic photoelectric conversion sections 11B, and four inorganic photoelectric conversion sections 11R (four blue pixels Pb and four red pixels Pr) are arranged vertically for one on-chip lens 19L.

FIGS. 5A, 5B, and 5C each schematically illustrate incident light (L) with respect to the organic photoelectric conversion section 11G and the inorganic photoelectric conversion sections 11B and 11R. In the present embodiment, as described above, one organic photoelectric conversion section 11G, four inorganic photoelectric conversion sections 11B, and four inorganic photoelectric conversion sections 11R are arranged for one on-chip lens 19L. This enables the inorganic photoelectric conversion sections 11B and 11R to acquire a signal for phase difference detection.

In addition, in the present embodiment, the multilayer wiring layer 70 is formed on the side of the second surface 11S2 of the semiconductor substrate 11. This enables the respective light receiving surfaces of the organic photoelectric conversion section 11G and the inorganic photoelectric conversion sections 11B and 11R to be arranged close to each other, thus making it possible to reduce variations in sensitivities between colors generated depending on a F-value of the on-chip lens 19L.

FIG. 6 is a plane view of an configuration example of the imaging element 1 in which a plurality of photoelectric conversion sections, to which the technology according to the present disclosure is applicable, (e.g., the inorganic photoelectric conversion sections 11B and 11R and the organic photoelectric conversion section 11G described above) are stacked. FIG. 6 illustrates an example of a planar configuration of the unit pixel P that configures the pixel section 1a illustrated in FIG. 20, for example, and represents the configuration example of the imaging element 1 in which the plurality of photoelectric conversion sections, to which the technology according to the present disclosure is applicable, are stacked.

The unit pixel P includes therein a photoelectric conversion region 1100 in which a red photoelectric conversion section (the inorganic photoelectric conversion section 11R in FIG. 3), a blue photoelectric conversion section (the inorganic photoelectric conversion section 11B in FIG. 3), and a green photoelectric conversion section (the organic photoelectric conversion section 11G in FIG. 3) (neither of which is illustrated in FIG. 6) that perform photoelectric conversion of light beams of respective wavelengths of R (Red), G (Green), and B (Blue) are stacked in three layers in the order of the green photoelectric conversion section, the blue photoelectric conversion section, and the red photoelectric conversion section, for example, from side of the light receiving surface (the light incident surface S1 in FIG. 3). Further, the unit pixel P includes the Tr group 1110, a Tr group 1120, and a Tr group 1130 as charge readout sections that read charges corresponding to light beams of the respective wavelengths of R, G, and B from the red photoelectric conversion section, the green photoelectric conversion section, and the blue photoelectric conversion section. The imaging element 1 performs, in one unit pixel P, spectroscopy in the vertical direction, i.e., spectroscopy of light beams of R, G, and B in respective layers as the red photoelectric conversion section, the green photoelectric conversion section, and the blue photoelectric conversion section stacked in the photoelectric conversion region 1100.

The Tr group 1110, the Tr group 1120, and the Tr group 1130 are formed on the periphery of the photoelectric conversion region 1100. The Tr group 1110 outputs, as a pixel signal, a signal charge corresponding to light of R generated and accumulated in the red photoelectric conversion section. The Tr group 1110 is configured by a transfer Tr (MOS FET) 1111, a reset Tr 1112, an amplification Tr 1113, and a selection Tr 1114. The Tr group 1120 outputs, as a pixel signal, a signal charge corresponding to light of B generated and accumulated in the blue photoelectric conversion section. The Tr group 1120 is configured by a transfer Tr 1121, a reset Tr 1122, an amplification Tr 1123, and a selection Tr 1124. The Tr group 1130 outputs, as a pixel signal, a signal charge corresponding to light of G generated and accumulated in the green photoelectric conversion section. The Tr group 1130 includes a transfer Tr 1131, a reset Tr 1132, an amplification Tr 1133, and a selection Tr 1134.

The transfer Tr 1111 is configured by (a source/drain region constituting) a gate G, a source/drain region S/D, and an FD (floating diffusion) 1115. The transfer Tr 1121 is configured by a gate G, a source/drain region S/D, and an FD 1125. The transfer Tr 1131 is configured by a gate G, (a source/drain region S/D coupled to) the green photoelectric conversion section of the photoelectric conversion region 1100, and an FD 1135. It is to be noted that the source/drain region of the transfer Tr 1111 is coupled to the red photoelectric conversion section of the photoelectric conversion region 1100, and that the source/drain region S/D of the transfer Tr 1121 is coupled to the blue photoelectric conversion section of the photoelectric conversion region 1100.

Each of the reset Trs 1112, 1132, and 1122, the amplification Trs 1113, 1133, and 1123, and the selection Trs 1114, 1134, and 1124 is configured by a gate G and a pair of source/drain regions S/D arranged to interpose the gate G therebetween.

The FDs 1115, 1135, and 1125 are coupled to the source/drain regions S/D serving as sources of the reset Trs 1112, 1132, and 1122, respectively, and are coupled to the gates G of the amplification Trs 1113, 1133 and 1123, respectively. A power supply Vdd is coupled to the common source/drain region S/D in each of the reset Tr 1112 and the amplification Tr 1113, the reset Tr 1132 and the amplification Tr 1133, and the reset Tr 1122 and the amplification Tr 1123. A VSL (vertical signal line) is coupled to each of the source/drain regions S/D serving as the sources of the selection Trs 1114, 1134, and 1124.

The technology according to the present disclosure is applicable to the above-described photoelectric conversion element.

(1-2. Method of Manufacturing Imaging Element)

The imaging element 1 of the present embodiment may be manufactured, for example, as follows.

FIGS. 7 and 8 illustrate the method of manufacturing the imaging element 1 in the order of steps. First, as illustrated in FIG. 7, the p-well 61, for example, is formed as a well of a first electrically-conductivity type in the semiconductor substrate 11, and the inorganic photoelectric conversion sections 11B and 11R of a second electrically-conductivity type (e.g., n-type) is formed in the p-well 61. The p+ region is formed in the vicinity of the first surface 11S1 of the semiconductor substrate 11. An n+ region serving as the floating diffusion FD1 is formed in the semiconductor substrate 11 to allow a portion thereof to be buried.

As illustrated in FIG. 7 as well, on the second surface 11S2 of the semiconductor substrate 11, n+ regions serving as the floating diffusions FD2 and FD3 are formed, and then, a gate insulating layer 62 and a gate wiring layer 64 including respective gates of the above-described Tr group 1110, and the like are formed. As a result, the vertical transistor Tr1 and various Tr group 1110 and the like are formed. Further, the multilayer wiring line 70 that includes the lower contact, the wiring layers 71 to 73 including the coupling section 71A, and the insulating layer 74 is formed on the second surface 11S2 of the semiconductor substrate 11.

As a base of the semiconductor substrate 11, for example, an SOI (Silicon on Insulator) substrate is used, in which the semiconductor substrate 11, an embedded oxide film (not illustrated), and a holding substrate (not illustrated) are stacked. Although not illustrated in FIG. 7, the embedded oxide film and the holding substrate are joined to the first surface 1S1 of the semiconductor substrate 11. After ion implantation, anneal processing is performed.

Next, a supporting substrate (not illustrated) or another semiconductor substrate, etc. is joined to the side of the second surface 11S2 (side of the multilayer wiring line 70) of the semiconductor substrate 11, and the substrate is turned upside down. Subsequently, the semiconductor substrate 11 is separated from the embedded oxide film and the holding substrate of the SOI substrate to expose the first surface 11S1 of the semiconductor substrate 11. The above steps may be performed by techniques used in common CMOS processes such as ion implantation and CVD (Chemical Vapor Deposition).

Next, as illustrated in FIG. 8, the semiconductor substrate 11 is processed from the side of the first surface 11S1 by dry-etching, for example, to form a ring-shaped opening 63H. As illustrated in FIG. 6, as for the depth, the opening 63H penetrates from the first surface 11S1 to the second surface 11S2 of the semiconductor substrate 11, and reaches, for example, the coupling section 71A.

Subsequently, as illustrated in FIG. 8, for example, the negative fixed charge layer 12A is formed on the first surface 11S1 of the semiconductor substrate 11 and a side surface of the opening 63H. Two or more kinds of films may be stacked as the negative fixed charge layer 12A. This makes it possible to further enhance the function as the hole accumulation layer. After the negative fixed charge layer 12A is formed, the dielectric layer 12B is formed.

Next, an electric conductor is buried in the opening 63H to form the through electrode 63. It is possible to use, as the electric conductor, for example, a metal material such as aluminum (Al), tungsten (W), titanium (Ti), cobalt (Co), hafnium (Hf), and tantalum (Ta), in addition to a doped silicon material such as PDAS (Phosphorus Doped Amorphous Silicon).

Subsequently, after formation of the pad section 13A on the through electrode 63, there is formed on the dielectric layer 12B and the pad section 13A, the interlayer insulating layer 14 in which the upper contact 13B and the pad section 13C that electrically couple the lower electrode 15 and the through electrode 63 (specifically, the pad section 13A on the through electrode 63) are provided on the pad section 13A.

Next, the lower electrode 15, the organic photoelectric conversion layer 16, the upper electrode 17, and the protective layer 18 are formed in this order on the interlayer insulating layer 14. Finally, the on-chip lens layer 19 is disposed, which includes the plurality of on-chip lenses 19L on the surface thereof. Thus, the imaging element 1 illustrated in FIG. 3 is completed.

It is to be noted that, in a case of forming another organic layer (e.g., an electron-blocking layer, etc.) on or under the organic photoelectric conversion layer 16, it is desirable to continuously form the other organic layer (by a vacuum-consistent process) in a vacuum process. In addition, the method of forming the organic photoelectric conversion layer 16 is not necessarily limited to the method using a vacuum deposition method; another method, for example, a spin-coating technique, a printing technique, or the like may be used.

(1-3. Method of Driving Imaging Element)

In the imaging element 1, when light enters the organic photoelectric conversion section 11G through the on-chip lens 19L, the light passes through the organic photoelectric conversion section 11G, the inorganic photoelectric conversion sections 11B and the 11R in this order, and photoelectrically converted for each light of green, blue, and red in the passing process. Hereinafter, description is given of a signal acquisition operation of each color.

(Acquisition of Green Signal by Organic Photoelectric Conversion Section 11G)

Green light of the light having entered the imaging element 1 is first selectively detected (absorbed) by the organic photoelectric conversion section 11G and is subjected to photoelectric conversion.

The organic photoelectric conversion section 11G is coupled to the gate G of the amplification Tr 1113 and the floating diffusion FD3 via the through electrode 63. Accordingly, holes of the electron-hole pairs generated in the organic photoelectric conversion section 11G are extracted from the side of the lower electrode 15, transferred to the side of the second surface 11S2 of the semiconductor substrate 11 via the through electrode 63, and accumulated in the floating diffusion FD3. At the same time, a charge amount generated in the organic photoelectric conversion section 11G is modulated into a voltage by the amplification Tr 1113.

In addition, a gate G of the reset Tr 1112 is disposed next to the floating diffusion FD3. As a result, the charges accumulated in the floating diffusion FD3 are reset by the reset Tr 1112.

Here, the organic photoelectric conversion section 11G is coupled not only to the amplification Tr 1113 but also to the floating diffusion FD3 via the through electrode 63, thus making it possible to easily reset the charges accumulated in the floating diffusion FD3 by the reset Tr 1112.

On the other hand, in a case where the through electrode 63 and the floating diffusion FD3 are not coupled to each other, it is difficult to reset the charges accumulated in the floating diffusion FD3, thus resulting in application of a large voltage to pull out the charges to the side of the upper electrode 17. Accordingly, there is a possibility that the organic photoelectric conversion layer 16 may be damaged. In addition, the structure that enables resetting in a short period of time leads to an increase in dark noises, resulting in a trade-off, which structure is thus difficult.

(Acquisition of Blue Signal and Red Signal by Inorganic Photoelectric Conversion Sections 11B and 11R)

Subsequently, of the light transmitted through the organic photoelectric conversion section 11G, blue light and red light are sequentially absorbed by the inorganic photoelectric conversion section 11B and the inorganic photoelectric conversion section 11R, respectively, and are subjected to photoelectric conversion. In the inorganic photoelectric conversion section 11B, electrons corresponding to the incident blue light are accumulated in an n region of the inorganic photoelectric conversion section 11B, and the accumulated electrons are transferred to the floating diffusion FD1. Similarly, in the inorganic photoelectric conversion section 11R, electrons corresponding to the incident red light are accumulated in an n region of the inorganic photoelectric conversion section 11R, and the accumulated electrons are transferred to the floating diffusion FD2 by a transfer transistor Tr.

The imaging element 1 of the present embodiment has a plurality of operation modes, e.g., three types of operation modes of a high-resolution mode, a high-sensitivity mode, and a high-speed mode. In the organic photoelectric conversion section 11G and the inorganic photoelectric conversion sections 11B and 11R, R/G/B signals are acquired as follows in each of the operation modes.

Description is given of the high-resolution mode. In the organic photoelectric conversion section 11G that acquires a green signal, as illustrated in FIG. 9A, signal charges are read from each of all the green pixels Pg. In the inorganic photoelectric conversion section 11B that acquires a blue signal and the inorganic photoelectric conversion section 11R that acquires a red signal, as illustrated in FIGS. 9B and 9C, FD addition is performed using four (2×2) pixels (blue pixels Pb and red pixels Pr) as one unit U. Thereafter, development processing is performed. It is possible, in the high-resolution mode, to acquire phase-matched signals among green pixels Pg, 2×2 blue pixels Pb, and 2×2 red pixels Pr. Therefore, R/G/B signals with no phase shift are obtained without signal processing in the unit pixel P.

Description is given of the high-sensitivity mode. In the organic photoelectric conversion section 11G that acquires a green signal, as illustrated in FIG. 11A, signal charges are read from each of all the green pixels Pg. In the inorganic photoelectric conversion section 11B that acquires a blue signal and the inorganic photoelectric conversion section 11R that acquires a red signal, as illustrated in FIGS. 11B and 11C, digital addition is performed using 16 (4×4) pixels (blue pixels Pb and red pixels Pr) as one unit U. At this time, each unit U of the inorganic photoelectric conversion section 11B and the inorganic photoelectric conversion section 11R that acquires a red signal is configured by 4×4 pixels shifted by 2×2 pixels from each other. Thereafter, the development processing is performed. As described above, each unit U of the inorganic photoelectric conversion section 11B and the inorganic photoelectric conversion section 11R that acquires a red signal is configured to be shifted by 2×2 pixels from each other. Therefore, in the high-sensitivity mode, there is a unit pixel P with no information of the blue pixel Pb or the red pixel Pr or no information of both the blue pixel Pb and the red pixel Pr in each unit pixel P. Therefore, in the development processing of the high-sensitivity mode, as illustrated in FIG. 12, a unit pixel P having, for example, a green signal and a blue signal complements a red signal from surrounding unit pixels P having a green signal and a red signal. This allows for R/G/B signals with no phase shift in the high-sensitivity mode.

Description is given of the high-speed mode. In the organic photoelectric conversion section 11G that acquires a green signal, as illustrated in FIG. 13A, signal charges are read from each of all the green pixels Pg. In the inorganic photoelectric conversion section 11B that acquires a blue signal and the inorganic photoelectric conversion section 13R that acquires a red signal, as illustrated in FIGS. 13B and 13C, digital addition is performed using four (2×2) pixels (blue pixels Pb and red pixels Pr) as one unit U. In the high-speed mode, thinning processing is thereafter performed, and the green signal, blue signal and red signal are acquired in a Bayer form as illustrated in FIG. 14. Finally, the development processing is performed for each unit pixel P. This allows for R/G/B signals with no phase shift in the high-speed mode.

It is to be noted that switching of addition modes used in the above-described respective operation modes may be performed as follows. In the imaging element 1A of the present embodiment, switches SW1, SW2, SW3, and SW4 are coupled, respectively, to the four blue pixels Pb and the four red pixels Pr (P1, P2, P3, and P4) provided in one unit pixel P. In an FD addition mode used in the high-resolution mode and the high-speed mode, as illustrated in FIG. 16, the switches SW1, SW2, SW3, and SW4 coupled, respectively, to the color pixels P1, P2, P3, and P4 are turned on to allow signals of the four color pixels P1, P2, P3, and P4 to be outputted as one pixel. In a digital addition mode used in the high-sensitivity mode, as illustrated in FIG. 17, one of the switches SW1, SW2, SW3, and SW4 coupled, respectively, to the color pixels P1, P2, P3, and P4 is turned on, while the remaining three switches are turned off to allow signals to be read for each of the color pixels P1, P2, P3, and P4 and then to be outputted as four pixels. Thereafter, signals for the four pixels are added in an ISP in a subsequent stage.

(1-4. Workings and Effects)

As described above, the solid-state imaging device such as the CMOS image sensor or the CCD image sensor is desired to have enhanced sensitivity. To that end, for example, a so-called vertical spectroscopic solid-state imaging device has been developed, in which an organic photoelectric conversion section having an organic photoelectric conversion film and two inorganic photoelectric conversion sections each having a p-n junction in a semiconductor substrate are stacked. In this vertical spectroscopic solid-state imaging device, R/G/B signals are able to be acquired from one pixel, thus making it possible to obtain higher resolution as compared with an imaging device in which respective color pixels (red pixel, green pixel, and blue pixel) having primary color filters of red, green, and blue are two-dimensionally arrayed.

However, in the vertical spectroscopic solid-state imaging device as described above, color mixture in RB spectroscopy is increased in the semiconductor substrate. Therefore, there is an issue that a color noise is increased, and the noise is amplified in a dark state, thus substantially deteriorating granular feeling. Examples of a method for improving the granular feeling include a method of using the high-sensitivity mode.

In the high-sensitivity mode in a typical imaging element 1000, as illustrated in FIG. 18A, signal charges are first read from each of all the green pixels Pg, in the organic photoelectric conversion section 1011G that acquires a green signal. In each of the inorganic photoelectric conversion section 11B that acquires a blue signal and the inorganic photoelectric conversion section 11R that acquires a red signal, digital addition is performed using four pixels (blue pixels Pb and red pixels Pr) in a 2×2 array as one unit U. At this time, each unit U of the inorganic photoelectric conversion section 11B and the inorganic photoelectric conversion section 11R are configured by 2×2 pixels shifted by 1×1 pixel from each other. Thereafter, pinning processing is performed as illustrated in FIG. 18B, and then demosaic processing is performed between the blue pixel Pb and the red pixel Pr to obtain RB signals as illustrated in FIG. 18C. Therefore, in the imaging element 1000, a phase shift occurs during operation of the green signal (G signal) and the RB signals as illustrated in FIG. 18D.

In contrast, in the imaging element 1 of the present embodiment, the inorganic photoelectric conversion sections 11B and 11R are formed to have the narrower pixel pitch (w) than the pixel pitch (W) of the organic photoelectric conversion section 11G, with respect to one pixel of the organic photoelectric conversion section 11G. Specifically, for example, four pixels in a 2×2 array of the inorganic photoelectric conversion sections 11B and 11R are each arranged with respect to one pixel of the organic photoelectric conversion section 11G. In the imaging element 1, a green signal is acquired from one pixel of the organic photoelectric conversion section 11G (green pixel Pg) during the above-described three operation modes (high-resolution mode, high-sensitivity mode, and high-speed mode), whereas the blue signal and the red signal are acquired by adding signals of four pixels in 2×2 or 16 pixels in 4×4 of the inorganic photoelectric conversion section 11B (blue pixels Pb) and the inorganic photoelectric conversion section 11R (red pixels Pr), respectively. Therefore, it is possible to acquire R/G/B signals with no phase shift.

As described above, in the imaging element 1 of the present embodiment, four (2×2) pixels of the inorganic photoelectric conversion sections 11B and 11R are each arranged with respect to one pixel of the organic photoelectric conversion section 11G. In each of the operation modes, the blue signal and the red signal are acquired by adding four pixels in 2×2 or 16 pixels in 4×4 of the inorganic photoelectric conversion section 11B (blue pixels Pb) and the inorganic photoelectric conversion section 11R (red pixels Pr) to one pixel of the organic photoelectric conversion section 11G (green pixel Pg) that acquires a green signal. In particular, the blue signal and the red signal are each acquired by adding signals from 16 pixels in 4×4 in the high-sensitivity mode, thus making it possible to reduce granular feeling in a dark state. That is, it is possible to provide an imaging element that achieves an enhancement in resolution and an improvement in granular feeling.

Next, description is given of a modification example of the present disclosure. In the following, components similar to those of the foregoing embodiment are denoted by the same reference numerals, and descriptions thereof are omitted as appropriate.

2. Modification Example

FIG. 19 illustrates a cross-sectional configuration of an imaging element (an imaging element 1B) according to a modification example of the present disclosure. Similarly to the photoelectric conversion element 10A, the imaging element 1B configures a CCD image sensor or a CMOS image sensor, etc. of a backside illumination type (backside light receiving type) (see FIG. 22). Similarly to the above-described imaging element 1A, the imaging element 1B is a vertical spectroscopic imaging element in which one organic photoelectric conversion section 20 that selectively detects and photoelectrically converts light beams of different wavelength bands and two inorganic photoelectric conversion sections 11B and 11R are stacked in the vertical direction. The imaging element 1B of the present modification example differs from the foregoing embodiment in that a lower electrode 21 includes a plurality of electrodes (a readout electrode 21A and an accumulation electrode 21B).

Similarly to the imaging element 1A in the foregoing embodiment, the organic photoelectric conversion section 20 is provided on the side of the back surface (first surface 11S1) of the semiconductor substrate 11. The inorganic photoelectric conversion sections 11B and 11R are each formed to be embedded in the semiconductor substrate 11, and are stacked in the thickness direction of the semiconductor substrate 11.

The organic photoelectric conversion section 20 has a configuration in which, for example, the lower electrode 21, the organic photoelectric conversion layer 16, and the upper electrode 17 are stacked in this order from the side of the first surface 11S1 of the semiconductor substrate 11. It is to be noted that an insulating layer 22 is provided between the lower electrode 21 and a charge accumulation layer 23. For example, the lower electrode 21 is formed separately for each imaging element 1B, and is configured by the readout electrode 21A and the accumulation electrode 21B, which are separated from each other with the insulating layer 22 interposed therebetween, although detailed descriptions thereof are given later. The insulating layer 22 on the readout electrode 21A is provided with an opening 22H, and the readout electrode 21A and the charge accumulation layer 23 are electrically coupled to each other via the opening 22H.

It is to be noted that, in the example illustrated in FIG. 19, the charge accumulation layer 23, the organic photoelectric conversion layer 16, and the upper electrode 17 are formed separately for each imaging element 1B, but may be provided as successive layers common to a plurality of imaging elements 1B, for example, similarly to the above-described imaging element 1A. For example, the fixed charge layer 12A, the dielectric layer 12B, and the interlayer insulating layer 14 are provided between the first surface 11S1 of the semiconductor substrate 11 and the lower electrode 21, similarly to the first embodiment. The protective layer 18 including a light-shielding film 51 is provided on the upper electrode 17. An optical member such as the on-chip lens layer 19 including the on-chip lens 19L is disposed on the protective layer 18.

As described above, the lower electrode 21 is configured by the readout electrode 21A and the accumulation electrode 21B, which are formed separately, and voltages are applied thereto independently of each other. The readout electrode 21A is provided for transferring charges (here, electrons) generated in the organic photoelectric conversion layer 16 to the floating diffusion FD3, and is coupled to the floating diffusion FD3 via an upper first contact 24A, a pad section 39A, the through electrode 63, the coupling section 71A, and the lower contact 75, for example. The accumulation electrode 21B is provided for accumulating electrons as signal charges, out of charges generated in the organic photoelectric conversion layer 16, in the charge accumulation layer 23, and for transferring the accumulated electrons to the readout electrode 21A. The accumulation electrode 21B is provided in a region opposed to and covering light receiving surfaces of the light receiving surface of the inorganic photoelectric conversion sections 11B and 11R formed in the semiconductor substrate 11. The accumulation electrode 21B is preferably larger than the readout electrode 21A, which makes it possible to accumulate a number of charges in the charge accumulation layer 23.

As described above, in the present modification example, the lower electrode 21 is divided into the readout electrode 21A and the accumulation electrode 21B, thus causing the voltages to be applied thereto independently of each other. This makes it possible, for the imaging element 1B, to accumulate the charges generated in the organic photoelectric conversion layer 16, in the charges accumulation layer 23 arranged between the lower electrode 21 and the organic photoelectric conversion layer 16, and makes it possible to read the accumulated charges into the floating diffusion FD3 appropriately via the readout electrode 21A. Thus, it is possible to completely deplete a charge accumulation section at the start of exposure, thus achieving an effect of improving captured image quality in addition to the effects of the foregoing embodiment.

3. Application Examples

Application Example 1

FIG. 20 illustrates, for example, an overall configuration of the imaging element 1 in which the imaging element 1 described in the foregoing embodiment is used for each pixel. The imaging element 1 is a CMOS imaging sensor. The imaging element 1 includes a pixel section 1a as an imaging area on the semiconductor substrate 11, and includes, for example, a peripheral circuit section 130 configured by a row scanner 131, a horizontal selector 133, a column scanner 134, and a system controller 132 in a peripheral region of the pixel section 1a.

The pixel section 1a includes, for example, a plurality of unit pixels P (corresponding to, e.g., the green pixel Pg of the imaging element 1) arranged two-dimensionally in matrix. To the unit pixels P, for example, pixel drive lines Lread (specifically, row selection lines and reset control lines) are wired on a pixel-row basis, and vertical signal lines Lsig are wired on a pixel-column basis. The pixel drive line Lread transmits a drive signal for reading of a signal from the pixel. One end of the pixel drive line Lread is coupled to an output terminal corresponding to each row in the row scanner 131.

The row scanner 131 is configured by a shift register, an address decoder, etc. The row scanner 131 is, for example, a pixel driver that drives the respective unit pixels P in the pixel section 1a on a row-unit basis. Signals outputted from the respective unit pixels P in the pixel row selectively scanned by the row scanner 131 are supplied to the horizontal selector 133 via the respective vertical signal lines Lsig. The horizontal selector 133 is configured by an amplifier, a horizontal selection switch, etc., that are provided for each vertical signal line Lsig.

The column scanner 134 is configured by a shift register, an address decoder, etc. The column scanner 134 sequentially drives the respective horizontal selection switches in the horizontal selector 133 while scanning the respective horizontal selection switches in the horizontal selector 133. As a result of the selective scanning by the column scanner 134, signals of the respective pixels to be transmitted via the respective vertical signal lines Lsig are sequentially outputted to horizontal signal lines 135, and are transmitted to the outside of the semiconductor substrate 11 through the horizontal signal lines 135.

A circuit part configured by the row scanner 131, the horizontal selector 133, the column scanner 134, and the horizontal signal lines 135 may be formed directly on the semiconductor substrate 11, or may be arranged in an external control IC. Alternatively, the circuit part may be formed on another substrate coupled with use of a cable, etc.

The system controller 132 receives a clock, data instructing an operation mode, etc., that are supplied from the outside of the semiconductor substrate 11. The system controller 132 also outputs data such as internal information of the imaging element 1. The system controller 132 further includes a timing generator that generates various timing signals, and performs drive control of peripheral circuits such as the row scanner 131, the horizontal selector 133, and the column scanner 134 on the basis of the various timing signals generated by the timing generator.

Application Example 2

The above-described imaging element 1 is applicable to any type of electronic apparatus having an imaging function, for example, a camera system such as a digital still camera and a video camera, and a mobile phone having the imaging function. FIG. 21 illustrates an outline configuration of a camera 2 as an example thereof. This camera 2 is, for example, a video camera that is able to photograph a still image or shoot a moving image. The camera 2 includes, for example, the imaging element 1, an optical system (optical lens) 310, a shutter device 311, a drive section 313 that drives the imaging element 1 and the shutter device 311, and a signal processing section 312.

The optical system 310 guides image light (incident light) from a subject to the pixel section lain the imaging element 1. The optical system 310 may be configured by a plurality of optical lenses. The shutter device 311 controls periods of light irradiation and light shielding with respect to the imaging element 1. The drive section 313 controls a transfer operation of the imaging element 1 and a shutter operation of the shutter device 311. The signal processing section 312 performs various types of signal processing on a signal outputted from the imaging element 1. An image signal Dout after the signal processing is stored in a storage medium such as a memory, or outputted to a monitor, etc.

Application Example 3

<Example of Practical Application to In-Vivo Information Acquisition System>

Further, the technology according to an embodiment of the present disclosure (present technology) is applicable to various products. For example, the technology according to an embodiment of the present disclosure may be applied to an endoscopic surgery system.

FIG. 22 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 22, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

The description has been given above of one example of the in-vivo information acquisition system, to which the technology according to an embodiment of the present disclosure is applicable. The technology according to an embodiment of the present disclosure is applicable to, for example, the image pickup unit 10112 of the configurations described above. This makes it possible to improve detection accuracy.

Application Example 4

<Example of Practical Application to Endoscopic Surgery System>

The technology according to an embodiment of the present disclosure (present technology) is applicable to various products. For example, the technology according to an embodiment of the present disclosure may be applied to an endoscopic surgery system.

FIG. 23 is a view depicting an example of a schematic configuration of an endoscopic surgery system to which the technology according to an embodiment of the present disclosure (present technology) can be applied.

In FIG. 23, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photoelectrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

FIG. 24 is a block diagram depicting an example of a functional configuration of the camera head 11102 and the CCU 11201 depicted in FIG. 23.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit

11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

The description has been given above of one example of the endoscopic surgery system, to which the technology according to an embodiment of the present disclosure is applicable. The technology according to an embodiment of the present disclosure is applicable to, for example, the image pickup unit 11402 of the configurations described above. Applying the technology according to an embodiment of the present disclosure to the image pickup unit 11402 makes it possible to improve detection accuracy.

It is to be noted that although the endoscopic surgery system has been described as an example here, the technology according to an embodiment of the present disclosure may also be applied to, for example, a microscopic surgery system, and the like.

Application Example 5

<Example of Practical Application to Mobile Body>

The technology according to an embodiment of the present disclosure (present technology) is applicable to various products. For example, the technology according to an embodiment of the present disclosure may be achieved in the form of an apparatus to be mounted to a mobile body of any kind. Non-limiting examples of the mobile body may include an automobile, an electric vehicle, a hybrid electric vehicle, a motorcycle, a bicycle, any personal mobility device, an airplane, an unmanned aerial vehicle (drone), a vessel, a robot, a construction machine, and an agricultural machine (tractor).

FIG. 25 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 25, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 25, an audio speaker 12061, a display section 12062, and an instrument panel 12063 are illustrated as the output device. The display section 12062 may, for example, include at least one of an on-board display and a head-up display.

FIG. 26 is a diagram depicting an example of the installation position of the imaging section 12031.

In FIG. 26, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 26 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

Description has been given hereinabove referring to the embodiment and the modification example as well as the application examples; however, the content of the present disclosure is not limited to the foregoing embodiment and the like, and various modifications may be made. For example, in the foregoing embodiment, the imaging element has a configuration in which four inorganic photoelectric conversion sections 11B and four inorganic photoelectric conversion sections 11R that detect blue light and red light, respectively, are stacked sequentially with respect to one organic photoelectric conversion section 11G that detects green light. However, the content of the present disclosure is not limited to such a structure.

For example, a configuration may be adopted, in which eight (eight pixels of) inorganic photoelectric conversion sections 11B and eight (eight pixels of) inorganic photoelectric conversion sections 11R that detect blue light and red light, respectively, are stacked sequentially with respect to one organic photoelectric conversion section 11G that detects green light. In addition, a configuration may be adopted, in which two organic photoelectric conversion sections and one inorganic photoelectric conversion section are stacked. In that case, the two organic photoelectric conversion sections may be formed at the same pixel pitch; alternatively, however, the organic photoelectric conversion section provided on side of the inorganic photoelectric conversion section may be formed narrower than a pixel pitch of the organic photoelectric conversion section arranged on the light incident side, as in the above-described inorganic photoelectric conversion sections 11B and 11R.

Further, the foregoing embodiment, etc. exemplifies the configuration of the backside illumination type imaging element; however, the content of the present disclosure is also applicable to an imaging element of a front-side illumination type. Further, the imaging element of the present disclosure need not include all of the components described in the foregoing embodiment, and may include any other layer, conversely.

It is to be noted that the effects described herein are merely exemplary and are not limitative, and may further include other effects.

It is to be noted that the present disclosure may have the following configurations.

(1)

An imaging element including:

a first photoelectric conversion section; and a second photoelectric conversion section, the first photoelectric conversion section and the second photoelectric conversion section being stacked in order from light incident side and selectively detecting and photoelectrically converting light beams of different wavelength bands, the second photoelectric conversion section being disposed at an interval narrower than a pixel pitch of the first photoelectric conversion section.

(2)

The imaging element according to (1), in which four pixels of the second photoelectric conversion section are disposed with respect to one pixel of the first photoelectric conversion section.

(3)

The imaging element according to (1), in which eight pixels of the second photoelectric conversion section are disposed with respect to one pixel of the first photoelectric conversion section.

(4)

The imaging element according to any one of (1) to (3), in which the first photoelectric conversion section includes an organic photoelectric conversion section formed using an organic material, and the second photoelectric conversion section includes an inorganic photoelectric conversion section formed to be embedded in a semiconductor substrate.

(5)

The imaging element according to (4), further including a third photoelectric conversion section that selectively detects and photoelectrically converts light of a wavelength band different from the first photoelectric conversion section and the second photoelectric conversion section, the third photoelectric conversion section being arranged between the first photoelectric conversion section and the second photoelectric conversion section, in which the third photoelectric conversion section includes an inorganic photoelectric conversion section formed to be embedded in the semiconductor substrate.

(6)

The imaging element according to (5), in which the third photoelectric conversion section is disposed at an interval narrower than the pixel pitch of the first photoelectric conversion section.

(7)

The imaging element according to (5) or (6), in which four pixels of the third photoelectric conversion section are disposed with respect to one pixel of the first photoelectric conversion section.

(8)

The imaging element according to (5) or (6), in which eight pixels of the third photoelectric conversion section are disposed with respect to one pixel of the first photoelectric conversion section.

(9)

The imaging element according to any one of (5) to (8), in which the first photoelectric conversion section performs photoelectric conversion of green light, and the second photoelectric conversion section and the third photoelectric conversion section each perform photoelectric conversion of red light or blue light.

(10)

The imaging element according to (4), further including a third photoelectric conversion section that selectively detects and photoelectrically converts light of a wavelength band different from the first photoelectric conversion section and the second photoelectric conversion section, the third photoelectric conversion section being arranged between the first photoelectric conversion section and the second photoelectric conversion section, in which the third photoelectric conversion section includes an organic photoelectric conversion section formed over the semiconductor substrate.

(11)

The imaging element according to (10), in which the third photoelectric conversion section is disposed at a pixel pitch similar to the first photoelectric conversion section.

(12)

An electronic apparatus including an imaging element, the imaging element including a first photoelectric conversion section, and a second photoelectric conversion section, the first photoelectric conversion section and the second photoelectric conversion section being stacked in order from light incident side and selectively detecting and photoelectrically converting light beams of different wavelength bands, the second photoelectric conversion section being disposed at an interval narrower than a pixel pitch of the first photoelectric conversion section.

(13)

A method of driving an imaging element including a first photoelectric conversion section and a second photoelectric conversion section that are stacked in order from light incident side and selectively detect and photoelectrically convert light beams of different wavelength bands, the second photoelectric conversion section being disposed at an interval narrower than a pixel pitch of the first photoelectric conversion section, the method including:

acquiring a color signal of first light using one pixel of the first photoelectric conversion section, and acquiring a color signal of second light of a wavelength band different from the first light by addition in a plurality of the second photoelectric conversion sections.

(14)

The method of driving the imaging element according to (13), in which the imaging element has, as operation modes, a high-resolution mode, a high-sensitivity mode, and a high-speed mode, and the acquiring of the color signal of the second light is performed by addition of four (2×2) pixels of the second photoelectric conversion section to one pixel of the first photoelectric conversion section in the high-resolution mode and the high-speed mode.

(15)

The method of driving the imaging element according to (13), in which the imaging element has, as operation modes, a high-resolution mode, a high-sensitivity mode, and a high-speed mode, and the acquiring of the color signal of the second light is performed by addition of 16 (4×4) pixels of the second photoelectric conversion section to one pixel of the first photoelectric conversion section in the high-sensitivity mode.

This application claims the benefit of Japanese Priority Patent Application JP2018-096530 filed with the Japan Patent Office on May 18, 2018, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. An imaging element, comprising:
a first photoelectric conversion section configured to acquire a color signal of first light; and
a second photoelectric conversion section configured to acquire a color signal of second light, wherein
each of the first photoelectric conversion section and the second photoelectric conversion section are configured to selectively detect and photoelectrically convert light beams of different wavelength bands,
a wavelength band of the first light is different from a wavelength band of the second light,
the color signal of the second light is acquired based on addition of four pixels of the second photoelectric conversion section to one pixel of the first photoelectric conversion section in a high-resolution mode and a high-speed mode,
the high-resolution mode and the high-speed mode are operation modes of the imaging element,
the first photoelectric conversion section and the second photoelectric conversion section are stacked in order from a light incident side, and
the second photoelectric conversion section is at an interval narrower than a pixel pitch of the first photoelectric conversion section.

2. The imaging element according to claim 1, wherein the four pixels of the second photoelectric conversion section are with respect to the one pixel of the first photoelectric conversion section.

3. The imaging element according to claim 1, wherein eight pixels of the second photoelectric conversion section are with respect to the one pixel of the first photoelectric conversion section.

4. The imaging element according to claim 1, wherein the first photoelectric conversion section comprises an organic photoelectric conversion section formed using an organic material, and the second photoelectric conversion section comprises an inorganic photoelectric conversion section formed to be embedded in a semiconductor substrate.

5. The imaging element according to claim 4, further comprising a third photoelectric conversion section configured to selectively detect and photoelectrically convert light of a wavelength band different from the first photoelectric conversion section and the second photoelectric conversion section, wherein
the third photoelectric conversion section being arranged between the first photoelectric conversion section and the second photoelectric conversion section, and
the third photoelectric conversion section comprises an inorganic photoelectric conversion section formed to be embedded in the semiconductor substrate.

6. The imaging element according to claim 5, wherein the third photoelectric conversion section is at an interval narrower than the pixel pitch of the first photoelectric conversion section.

7. The imaging element according to claim 5, wherein four pixels of the third photoelectric conversion section are with respect to one pixel of the first photoelectric conversion section.

8. The imaging element according to claim 5, wherein eight pixels of the third photoelectric conversion section are with respect to one pixel of the first photoelectric conversion section.

9. The imaging element according to claim 5, wherein
the first photoelectric conversion section is further configured to execute photoelectric conversion of green light,
the second photoelectric conversion section is further configured to execute photoelectric conversion of red light, and
the third photoelectric conversion section is further configured to execute photoelectric conversion of blue light.

10. The imaging element according to claim 4, further comprising a third photoelectric conversion section configured to selectively detect and photoelectrically convert light of a wavelength band different from the first photoelectric conversion section and the second photoelectric conversion section, wherein
the third photoelectric conversion section is arranged between the first photoelectric conversion section and the second photoelectric conversion section, and
the third photoelectric conversion section comprises an organic photoelectric conversion section over the semiconductor substrate.

11. The imaging element according to claim 10, wherein the third photoelectric conversion section is at a pixel pitch similar to the pixel pitch of the first photoelectric conversion section.

12. An electronic apparatus, comprising:
an imaging element, the imaging element including:
a first photoelectric conversion section configured to acquire a color signal of first light, and
a second photoelectric conversion section configured to acquire a color signal of second light, wherein
each of the first photoelectric conversion section and the second photoelectric conversion section are configured to selectively detect and photoelectrically convert light beams of different wavelength bands,
a wavelength band of the first light is different from a wavelength band of the second light,
the color signal of the second light is acquired based on addition of four pixels of the second photoelectric conversion section to one pixel of the first photoelectric conversion section in a high-resolution mode and a high-speed mode,
the high-resolution mode and the high-speed mode are operation modes of the imaging element,
the first photoelectric conversion section and the second photoelectric conversion section are stacked in order from a light incident side, and
the second photoelectric conversion section is at an interval narrower than a pixel pitch of the first photoelectric conversion section.

13. A method of driving an imaging element including a first photoelectric conversion section and a second photoelectric conversion section, wherein the method comprising:

acquiring, by the first photoelectric conversion section, a color signal of first light; and acquiring, by the second photoelectric conversion section, a color signal of second light, wherein
- each of the first photoelectric conversion section and the second photoelectric conversion section are configured to selectively detect and photoelectrically convert light beams of different wavelength bands,
- a wavelength band of the first light is different from a wavelength band of the second light,
- the color signal of the second light is acquired based on addition of four pixels of the second photoelectric conversion section to one pixel of the first photoelectric conversion section in a high-resolution mode and a high-speed mode,
- the high-resolution mode and the high-speed mode are operation modes of the imaging element,
- the first photoelectric conversion section and the second photoelectric conversion section are stacked in order from a light incident side, and
- the second photoelectric conversion section is at an interval narrower than a pixel pitch of the first photoelectric conversion section.

14. The method of driving the imaging element according to claim 13, wherein
- the color signal of the second light is further acquired based on addition of 16 (4×4) pixels of the second photoelectric conversion section to one pixel of the first photoelectric conversion section in a high-sensitivity mode, and
- the high-sensitivity mode is an operation mode of the imaging element.

* * * * *